United States Patent
Alfini et al.

(10) Patent No.: US 12,036,285 B2
(45) Date of Patent: Jul. 16, 2024

(54) IMMUNOGENIC CONJUGATES AND USE THEREOF

(71) Applicant: GLAXOSMITHKLINE BIOLOGICALS, S.A., Rixensart (BE)

(72) Inventors: Renzo Alfini, Siena (IT); Francesca Micoli, Siena (IT); Allan James Saul, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 1401 days.

(21) Appl. No.: 16/462,624

(22) PCT Filed: Nov. 23, 2017

(86) PCT No.: PCT/EP2017/080145
§ 371 (c)(1),
(2) Date: May 21, 2019

(87) PCT Pub. No.: WO2018/096007
PCT Pub. Date: May 31, 2018

(65) Prior Publication Data
US 2023/0137821 A1  May 4, 2023

(30) Foreign Application Priority Data

Nov. 25, 2016 (GB) .................................. 1619946
Jul. 27, 2017 (GB) .................................. 1712096

(51) Int. Cl.
*A61K 47/64* (2017.01)
*A61K 47/54* (2017.01)
*A61K 47/69* (2017.01)
*A61P 31/04* (2006.01)

(52) U.S. Cl.
CPC .......... *A61K 47/646* (2017.08); *A61K 47/549* (2017.08); *A61K 47/6911* (2017.08); *A61P 31/04* (2018.01)

(58) Field of Classification Search
CPC ............................ A61K 39/385; A61K 39/112
IPC ....................................... A61K 39/385,39/0275
See application file for complete search history.

(56) References Cited

U.S. PATENT DOCUMENTS

2016/0263213 A1* 9/2016 MacLennan ............ A61P 31/04

FOREIGN PATENT DOCUMENTS

| JP | H11322793 A | 11/1999 |
|---|---|---|
| JP | 2004527235 A | 9/2004 |
| JP | 2014520801 A | 8/2014 |
| JP | 2015518845 A | 7/2015 |
| JP | 2019527842 A | 10/2019 |
| WO | WO-2002062378 A2 | 8/2002 |
| WO | 2006123164 A2 | 11/2006 |
| WO | 2013/006055 A1 | 1/2013 |
| WO | 2013174832 A1 | 11/2013 |
| WO | 2016083583 A1 | 6/2016 |
| WO | 2016/184860 A1 | 11/2016 |
| WO | 2018010059 A1 | 1/2018 |
| WO | 2018096007 A2 | 5/2018 |
| WO | 2018096013 A1 | 5/2018 |

OTHER PUBLICATIONS

Alves, et al., "Emerging therapeutic delivery capabilities and challenges utilizing enzyme/protein packaged bacterial vesicles." Therapeutic Delivery; 2015; pp. 873-887; vol. 6 (7).
Devi S J N, et al., "Binding diversity of monoclonal antibodies to alpha(2-8) polysialic acid conjugated to outer membrane vesicle via adipic acid dihydrazide" FEMS Immunology and Medical Microbiology; 1996; pp. 211-220; vol. 14 (4).
Devi S J N, et al., "Preclinical Evaluation of Group B Neisseria Meningitidis and *Escherichia coli* K92 Capsular Polysaccharide-Protein Conjugate Vaccines in Juvenile Rhesus Monkeys." Infection and Immunity; 1997; pp. 1045-1052; vol. 65(3).
Farjah, et al., "Immunological evaluation of an alginate-based conjugate as a vaccine candidate against Pseudomonas aeruginosa" Acta Pathologica, Microbiologica et Immunologica Scandinavica. 2014; pp. 175-183; vol. 123.
Fukasawa L O, et al., "Neisseria meningitidis serogroup C polysaccharide and serogroup B outer membrane vesicle conjugate as a bivalent meningococcus vaccine candidate." Vaccine; 1999; pp. 2951-2958; vol. 17(23-24).
Fukasawa, et al., "Adjuvant can improve protection induced by OMV vaccine agaisnt Neisseria meningitidis serogroups B/C in neonatal mice." FEMS Immunology and Medical Microbiology; 2004; pp. 205-210; vol. 41(3).
Fukasawa, et al., "Optimization of the Conjugation Method for a Serogropup B/C Meningococcal Vaccine." Biotechnology and Applied Biochemi. 2006; pp. 141-146; vol. 45 (3).
Price, et al., "Glycoengineered Outer Membrane Vesicles: A Novel Platform for Bacterial Vaccines" Scientific Reports; 2016; vol. 6(1).
Siadat, et al., "Evaluation of Serum Bactericidal Activity Specific for Neisseria meningitidis Serogroup A and B: Effect of Immunization with Neisseria meningitidis Serogroup A Polysachharide and Serogroup B Outer Membrance Vesicle Conjugate as a Bivalent Meningococcus Vaccine Candidate" Research Journal of Microbiology; 2007; pp. 436-444; vol. 2(5).
Siadat, et al., "Preparation and Evaluation of a New Lipopolysaccharide-based Conjugate as a Vaccine Candidate for Brucellosis." Osong Public Health and Research Perspectives; 2015; pp. 9-13; vol. 6(1).
Zhang, et al., "Improving the immunogenicity of a trivalent Neisseria meningitidis native outer membrane vesicle vaccine by genetic modification." Vaccine; 2016; pp. 4250-4256; vol. 34(35).

(Continued)

Primary Examiner — Walter E Webb

(57) ABSTRACT

The provided technology is in the field of conjugating native, non-detergent extracted, outer membrane vesicles (nOMV) to antigens to form nOMV-antigen conjugates, which are particularly useful for immunogenic compositions and immunisation; processes for the preparation and use of such conjugates is also provided.

21 Claims, 11 Drawing Sheets

Specification includes a Sequence Listing.

(56) References Cited

OTHER PUBLICATIONS

Zollinger, et al., "Bactericidal antibody responses of juvenile rhesus monkeys immunized with group B Neisseria meningitidis capsular polysaccharide-protein conjugate vaccines." Infection and Immunity; 1997; pp. 1053-1060, vol. 65.

Van De Waterbeemd, et al, "Quantitative Proteomics Reveals Distinct Differences in the Protein Content of Outer Membrane Vesicle Vaccines," Journal of Proteome Research (2013); vol. 12, pp. 1898-1908.

* cited by examiner

IMMUNOGENIC CONJUGATES AND USE THEREOF

REFERENCE TO SEQUENCE LISTING

The content of the electronically submitted sequence listing (Name: VB66222_Sec_Lstg.txt; 51,082 bytes; and Created Jun. 14, 2019 was originally submitted in the International Application No. PCT/EP2017/080145 filed Nov. 23, 2017 and is incorporated herein by reference in its entirety.

This invention is in the field of conjugating "native", non-detergent extracted, outer membrane vesicles (nOMV) to antigens, to form nOMV-antigen conjugates, particularly useful for immunisation.

BACKGROUND ART

Conjugation of antigens to carriers is an established procedure for improving immunogenicity, especially for saccharides. For instance, bacterial capsular saccharides are naturally T-cell independent antigens which give rise to an immune response that lacks several important properties. Conjugation to a carrier moiety converts these saccharides to T-cell dependent antigens which can then produce an immunological memory effect, and also elicit effective immune responses in young children.

One known source of protein carrier in such conjugates is the Outer Membrane Protein Complex (OMPC) from *N. meningitidis* serogroup B (e.g. see EP-0467714, Merck & co.), which has been included as the carrier in approved *H. influenzae* B conjugate vaccines. OMPC has also been used as the carrier in protein conjugates. According to the prior art, OMPC is conjugated to an antigen via a protein residue, which may be activated or chemically modified in order to better perform the conjugation with the selected antigen.

Wu et al. (PNAS USA 2006; 103(48): 18243-18248) report that conjugation of Pfs25H (a human malarial transmission-blocking protein) to OMPC resulted in a Pfs25H-OMPC conjugate vaccine that was >1,000 times more potent in generating anti-Pfs25H ELISA reactivity in mice than a similar dose of Pfs25H alone. Conjugation of OMPC to Pfs25H protein can be achieved by reacting maleimide-activated Pfs25H with thiolated outer membrane proteins within OMPC (for a general reference see e.g. WO2006/124712), as shown in Scheme 1.

Scheme 1

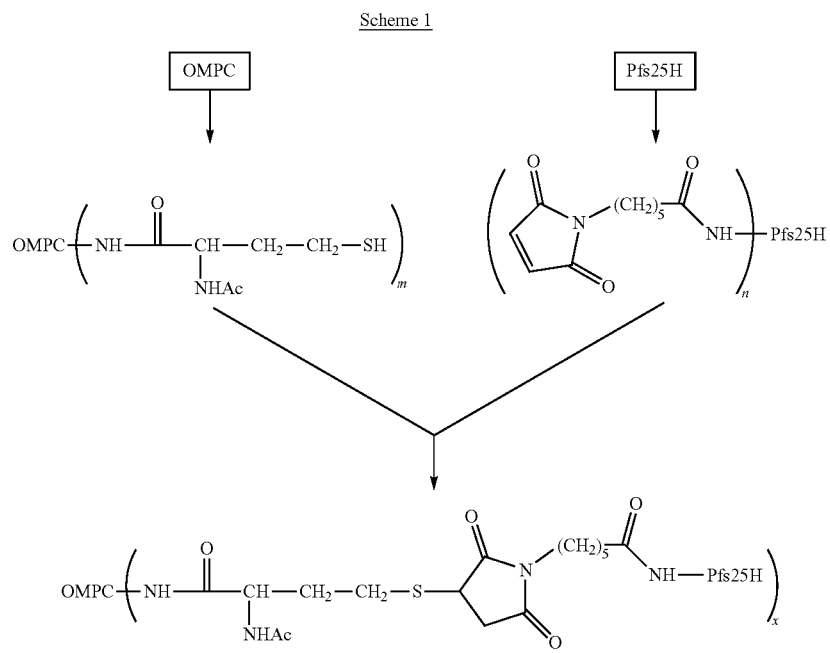

Even if the process can represent a valid synthetic route, the considered vesicles may be difficult to obtain in a pure form, and they are usually collected via laborious processes. Also, the connection with the selected antigen requires the presence and the activation of a suitable vesicle protein, thus posing an additional challenge in light of the use of detergents or chemicals during the vesicle isolation, which can alter the surface proteins composition. Therefore, there is still the need to provide new conjugates useful as immunogenic compounds which overcome the problems of the prior art, and that are achievable by an easy and convenient procedure.

The Applicant has now found that when nOMVs are connected to selected antigens via saccharide moieties, the thus obtained conjugates are endowed with a remarkable immunogenicity and can be obtained by a reliable and convenient process, as herein below described in more details.

SUMMARY OF THE INVENTION

In a first aspect, the invention refers to an immunogenic nOMV-antigen conjugate, comprising a native, outer membrane vesicle (nOMV) obtained by a detergent free process, having at least a native surface saccharide moiety connected to at least a foreign selected antigen.

In a further aspect, the invention refers to a process for preparing said conjugate, comprising the steps of:
 i) activating at least a nOMV saccharide moiety, generally bond to the nOMV surface, and i) connecting the thus obtained activated saccharide to at least one selected antigen.

According to a preferred embodiment, the nOMV-surface bond saccharides are activated by oxidation, and then connected with the selected antigens, more preferably under reductive amination conditions.

In an additional aspect, the invention also refers to the above conjugate for use as a medicament, particularly as an immunogenic compound, or for the preparation of an immunogenic composition or vaccine.

Still in a further aspect, the invention refers to an immunogenic composition or a vaccine, comprising the above indicated conjugate and at least one pharmaceutically acceptable carrier or adjuvant; and to a method for raising an immune response in a vertebrate, comprising the administration of said composition or vaccine.

In a further aspect, the invention also refers to the use of nOMV for the preparation of immunogenic conjugates.

DETAILED DESCRIPTION OF THE INVENTION

Figure 1:
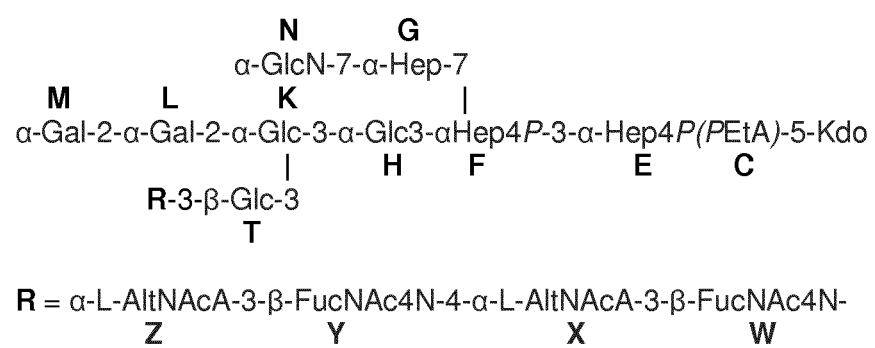
FIG. 1 shows the —OAg structures for *S. sonnei*.

To facilitate an understanding of the present invention, a number of terms and phrases are defined below. Art-recognized synonyms or alternatives of the following terms and phrases (including past, present, etc. tenses), even if not specifically described, are contemplated.

As used in the present disclosure and claims, the singular forms "a," "an," and "the" include plural forms unless the context clearly dictates otherwise; i.e., "a" means "one or more" unless indicated otherwise.

The terms "about" or "approximately" mean roughly, around, or in the regions of. The terms "about" or "approximately" further mean within an acceptable contextual error range for the particular value as determined by one of ordinary skill in the art, which will depend in part on how the value is measured or determined, i.e. the limitations of the measurement system or the degree of precision required for a particular purpose, e.g. the amount of a nutrient within a feeding formulation. When the terms "about" or "approximately" are used in conjunction with a numerical range, it modifies that range by extending the boundaries above and below the numerical values set forth. For example "between about 0.2 and 5.0 mg/ml" means the boundaries of the numerical range extend below 0.2 and above 5.0 so that the particular value in question achieves the same functional result as within the range. For example, "about" and "approximately" can mean within 1 or more than 1 standard deviation as per the practice in the art. Alternatively, "about" and "approximately" can mean a range of up to 20%, preferably up to 10%, more preferably up to 5%, and more preferably up to 1% of a given value.

The term "and/or" as used in a phrase such as "A and/or B" is intended to include "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless specified otherwise, all of the designations "A %-B %," "A-B %," "A % to B %," "A to B %," "A %-B," "A % to B" are given their ordinary and customary meaning. In some embodiments, these designations are synonyms.

The terms "substantially" or "substantial" mean that the condition described or claimed functions in all important aspects as the standard described. Thus, "substantially free" is meant to encompass conditions that function in all important aspects as free conditions, even if the numerical values indicate the presence of some impurities or substances. "Substantial" generally means a value greater than 90%, preferably greater than 95%, most preferably greater than 99%. Where particular values are used in the specification and in the claims, unless otherwise stated, the term "substantially" means with an acceptable error range for the particular value.

An "effective amount" means an amount sufficient to cause the referenced effect or outcome. An "effective amount" can be determined empirically and in a routine manner using known techniques in relation to the stated purpose.

As used herein, "heterologous" means the two or more referenced molecules or structures are derived from a different organism. For example, a heterologous antigen is one that is derived from a different organism than the nOMV vesicle to which it is appended. "Homologous" as used herein means the two or more referenced molecules or structures are derived from the same organism.

As used herein, "foreign" means the two or more referenced molecules or structures are not naturally associated with each other. For example, a selected antigen that is herein intended to be "foreign to" a nOMV surface saccharide herein means the antigen is not naturally or innately conjugated to the surface saccharide and is, therefore, not naturally conjugated to the nOMV molecule even though the antigen and the saccharide (or nOMV molecule) may originate from the same organism. In this way, a foreign antigen is not necessarily a heterologous antigen but a heterologous antigen is a foreign antigen.

"Sequence identity" can be determined by the Smith-Waterman homology search algorithm as implemented in the MPSRCH program (Oxford Molecular), using an affine gap search with parameters gap open penalty=12 and gap extension penalty=1, but is preferably determined by the Needleman-Wunsch global alignment algorithm (see e.g. Rubin (2000) Pediatric. Clin. North Am. 47:269-285), using default parameters (e.g. with Gap opening penalty=10.0, and with Gap extension penalty=0.5, using the EBLOSUM62 scoring matrix). This algorithm is conveniently implemented in the needle tool in the EMBOSS package. Where the application refers to sequence identity to a particular SEQ ID, the identity is intended to be calculated over the entire length of that SEQ ID.

The term "w/w %" indicates the weight percentage of a given component, over a different component or over the whole content of a composition, as indicated.

Analogously, the term "% v/v" indicates the volume percentage of a given component, over a different component or over the whole content of a composition, as indicated.

The term "—OAg" (O-antigen) is used within the present invention to indicate an antigen functionality present in the lipopolysaccharides (LPS) or lipooligosaccharides (LOS) on the surface of the considered nOMV, useful for the conjugation with a proper antigen (generally indicated as Ag) according to the invention. In more details, the LPS are generally formed by three different portions, known as: lipidA (responsible for the toxicity of LPS), core oligosaccharide and the —OAg chain, a repetitive glycan polymer and major contributor to the serological specificity of bacteria.

The term "linear or branched $C_1$-$C_x$ alkyl or alkenyl group" comprises in its meaning a divalent satured or unsaturated linear or branched alky or alkenyl group having 1 to x carbon atoms. For instance, the term divalent $C_1$-$C_{10}$ alkyl or alkenyl group comprises in its meaning a divalent satured or unsaturated alky or alkenyl group having 1 to 10 carbon atoms such as methyl, ethyl, vinyl, allyl and the like.

As herein used, the term "saccharide (or sugar) moiety" comprises in its meaning mono saccharides, as well as polysaccharide units. It will be appreciated that saccharide moieties can exist in open and closed (ring) form and that, while closed forms are shown in structural formulae herein, open forms are also encompassed by the invention. Similarly, it will be appreciated that saccharide moieties can exist in pyranose and furanose forms and that, while pyranose forms are shown in structural formulae herein, furanose forms are also encompassed. Different anomeric forms of saccharide moieties are also encompassed.

The term "oligosaccharide" comprises in its meaning polysaccharides having from 3 to 10 monosaccharide units.

Unless otherwise provided, the term "polypeptide" refers to polypeptides of any length capable to act as a selected antigen. The amino acid polymer forming the polypeptide of the invention, may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labelling component. Also included within the definition are, for example, polypeptides containing one or more analogues of an amino acid (including, for example, unnatural amino acids, etc.), as well as other modifications known in the art. Polypeptides can occur as single chains or associated chains.

"Average molecular weight" is intended to indicate the average molecular weight obtained by the ordinary arithmetic mean or average of the molecular masses of the individual component, e.g. aminoacids in case of polypeptide derivatives.

The term "capsular polysaccharides/saccharides" (CPSs) indicates those saccharides which can be found in the layer that lies outside the cell envelope of bacteria, thus being part of the outer envelope of the bacterial cell itself. CPSs are expressed on the outermost surface of a wide range of bacteria, and in some cases even in fungi.

Unless otherwise provided, the term "conjugation" indicates the connection or linkage of the subjected entities, particularly referred to the nOMV and the selected antigen moieties.

By "immunologically effective amount", it is meant that the administration of that amount to an individual, either in a single dose or as part of a series, is effective for treatment or prevention. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

The term "nOMVs" herein indicates vesicle isolated from the medium or sheared from cells, and they are intact membrane vesicles not exposed to detergents or denaturing agents, i.e. not detergent extracted. The nOMVs of the invention present the outer membrane proteins (OMP) and lipopolysaccharide (LPS) in their native conformation and correct orientation in the natural membrane environment, and usually lack the cytoplasmatic components.

On the contrary, the term "OMV" or "dOMV" encompasses a variety of proteoliposomic vesicles obtained by disruption of the outer membrane of a Gram-negative bacterium typically by a detergent extraction process to form vesicles therefrom. Outer membrane protein complexes (e.g. OMPC from *Neisseria meningitidis*) may be considered in such definition, since having three dimensional structure and composition similar to dOMV, and being isolated via detergent extraction procedures (see e.g. EP0467714, U.S. Pat. Nos. 4,271,147, 4,459,286 and 4,830,852). The detergent extraction process removes LPS and phospholipids, together with immunoprotective lipoproteins. Such removal changes the native vesicle structure and promotes aggregation. The aggregation may lead to consequent issues in terms of process development (yield, consistency of production and stability). Differently from nOMVs, characterized by defined homogeneous size distribution (typically in the range 20-250 nm, measured by Dynamic Light Scattering DLS technique), the dOMVs have an undefined heterogeneous size distribution (usually in the range 550-5500 nm as measured by Dynamic Light Scattering DLS technique) caused by detergent-induced vesicle aggregation (see for a general reference, Vaccine 28, 2010, 4810). The detergent extraction process also causes contamination of OMV containing composition (e.g. vaccines) with cytoplasmic proteins as a result of bacterial cell lysis.

According to prior art methodologies, dOMVs and nOMVs may be analysed and described in terms of size, shape and overall appearance of impurities or contaminating non-OMV materials (like vesicle aggregates or detergent residues in case of dOMVs) using the Transmission Electron Microscopy (TEM). For detailed references regarding the differences between dOMVs and nOMVs see e.g. van de Waterbeemd (2013) J. Prot. Res. "Quantitative Proteomics Reveals Distinct Differences in the Protein Content of Outer Membrane Vesicle Vaccines"; and J. Klimentova et al. Microbiological Research 170 (2015) 1-9 "Methods of isolation and purification of the outer membrane vesicles from gram-negative bacteria".

As above indicated, in a first aspect, the invention refers to a conjugate comprising a selected antigen connected to a saccharide moiety present on the surface of a non-detergent extractive native Outer Membrane Vesicle (nOMV). Of note, the nOMVs in accordance with the present invention are collected and isolated substantially without the use of detergents, differently for instance from dOMVs of the prior art obtained via a deoxycholate extraction or using zwitterionic detergents like Empigen BB (see e.g. U.S. Pat. No. 4,707,543) or similar. On the contrary, it has to be highlighted that a detergent extraction step may be undesirable in the present invention, for a series of reasons, among which the fact that a detergent would reduce the amount of lipopolysaccharide (LPS)/lipooligosaccharide (LOS) present on the vesicle, which can be indeed useful for the conjugation with the selected antigen as herein below described.

In further details, the nOMVs are naturally-occurring membrane vesicles that form spontaneously during bacterial growth and are released into culture medium. They can be obtained e.g. by culturing bacteria in broth culture medium, separating whole cells from the smaller nOMVs in the broth culture medium (e.g. by filtration or by low-speed centrifugation to pellet only the cells and not the smaller vesicles), and then collecting the nOMVs from the cell-depleted medium (e.g. by filtration, by differential precipitation or aggregation, by high-speed centrifugation to pellet the vesicles). Strains for use in production of nOMVs can generally be selected on the basis of the amount of nOMVs produced in culture. The present nOMVs are characterised by the fact of being collected and isolated following a detergent-free procedure. Preferably, the present nOMVs are released into the fermentation broth and are purified using a centrifugation and subsequent filtration step (for a general reference see e.g. Clin Vaccine Immunol. 2016 April; 23(4): 304-314). Still preferably, the present nOMVs are released into the fermentation broth and are purified using the following two consecutive Tangential Flow Filtration (TFF) steps: (i) a microfiltration in which the culture supernatant containing the nOMV is separated from the bacteria, and (ii) an ultrafiltration in which the nOMV are separated from soluble proteins (for a general reference see e.g. PLoS One. 2015; 10(8): e0134478). The thus obtained nOMVs can then directly be used within the present invention without additional purification/isolation steps. The presently considered nOMVs have a preferred size distribution comprised from 20 to 250 nm, measured by Dynamic Light Scattering DLS technique.

According to some embodiments, the nOMVs are prepared from wild-type bacteria or from bacteria which have been genetically manipulated generally to increase immunogenicity (e.g. to hyper-express immunogens), to reduce toxicity, to inhibit capsular saccharide synthesis, to down-regulate immunodominant antigen expression, and the like. They also may be prepared from hyperblebbing strains. The nOMVs of the invention may also express exogenous proteins on their surface and they may be endotoxin-depleted.

Preferably, the nOMVs to be used in the present invention are produced from genetically-modified bacterial strains that are mutated to enhance vesicle production, and optionally also to remove or modify antigens (e.g. lipid A) and/or to over-express homologous antigens or antigens from other organisms. Said preferred nOMVs are also known as Generalized Modules of Membrane Antigens (GMMA) as e.g. described in PLoS One. 2015; 10(8): e0134478.

Enhanced spontaneous generation of vesicles can be achieved, for example, by targeted deletion of proteins involved in maintenance of membrane integrity. It has been observed that the outer surface of nOMVs substantially corresponds to the outer surface of the bacterium from which they are derived, preserving the membrane antigens (including e.g. lipopolysaccharides, lipooligosaccharides and lipoproteins) in the context of the membrane. Advantageously, the nOMVs used in the invention (unlike detergent-extracted dOMVs) retain these outer membrane components in their native conformation and correct orientation, better preserving immunogenicity against the bacterial strain from which they are derived.

Generally, the nOMVs for use in the present invention may be prepared from any suitable bacterium, where preferred bacteria include, but are not limited to: *Neisseria* (e.g. in particular *N. meningitidis* of any serogroups including A, B, C, X, Y or W135, or from a non-pathogenic *Neisseria*), *Shigella* (such as *S. sonnei*, *S. flexneri*, *dysenteriae* or *boydii*), *Salmonella enterica* serovars (such as Paratyphi A, B or C, *Enteritidis*, *Typhi* or Typhimurium), *Haemophilus influenzae* (e.g. non-typable *H. influenzae*), *Vibrio cholerae*, *Bordetella pertussis*, *Mycobacterium smegmatis*, *Mycobacterium bovis* BCG, *Escherichia coli*, *Bacteroides* (including *Porphyromonas*), *Pseudomonas aeruginosa*, *Helicobacter pylori*, *Brucella melitensis Campylobacter jejuni*, *Actinobacillus actinomycetemcomitans*, *Xenorhabdus nematophilus*, *Moraxella catarrhalis*, or *Borrelia burgdorferi*.

Particularly preferred bacteria are selected from at least one of: *S. sonnei*, *S. flexneri*, *Salmonella* bacterium, and meningococcus, particularly meningococcus serogroup B.

Virulent *Shigella* strains possess a 220 kb plasmid that mediates virulence properties. This "virulence plasmid" has been shown to encode the genes for several aspects of *Shigella* virulence, including adhesins for target epithelial cells, the invasion plasmid antigens, virF, virG, and the like. A *Shigella* used with the invention may or may not possess a virulence plasmid. Absence of the plasmid can stabilise the strain during industrial culture, attenuate the strain by removing virulence factors (thereby increasing safety of manufacture), avoid the presence of the ShET-2 enterotoxin (encoded by the ospD3 or sen gene on the plasmid), and avoid the presence of msbB2 which is a second copy of the msbB gene responsible for acylation of lipid A. Absence of the virulence plasmid may also disrupt the lipopolysaccharide. However, the biosynthesis genes for the —OAg should preferably be retained, either by maintenance of a mutated virulence plasmid, or by inclusion in a further plasmid or cloning into the bacterial chromosome.

As far as *Salmonella* bacterium is concerned, a particularly preferred strain is selected from:

*Salmonella Typhimurium, Salmonella Enteritidis* and *Salmonella* Paratyphi A.

Meningococcus bacteria nOMVs are also preferred. Such vesicles can be prepared from any meningococcal strain. The vesicles are preferably prepared from a serogroup B strain, but it is also preferred to prepare them from serogroups other than B, such as one of: A, C, W135 or Y, according to procedures known in the art. The strain may be of any serotype (e.g. 1, 2a, 2b, 4, 14, 15, 16, etc.), any serosubtype (e.g. P1.4), and any immunotype (e.g. L1; 12; L3; L3,7; L3,7,9; L10; etc.). The meningococci may be from any suitable lineage, including hyperinvasive and hypervirulent lineages, preferably any of the following seven hypervirulent lineages: subgroup I; subgroup III; subgroup IV-1; ET-5 complex; ET-37 complex; A4 cluster; lineage 3. Most preferably, OMVs are prepared from the strain NZ98/254, or another strain with the P1.4 PorA serosubtype.

In another embodiment, bacteria for preparing nOMVs useful for the invention may be mutant strains which have been manipulated e.g. to enhance vesicle production, to express one or more desired antigen(s), and/or to knockout or modify an undesired gene (e.g. one which encodes a toxin or which encodes an enzyme involved in generating a toxic product, such as endotoxin).

In this direction, other preferred nOMVs for the invention are produced by a *Salmonella* bacterium, particularly a *S. Typhimurium* (also known as *Salmonella enterica* serovar Typhimurium) which does not express a functional ToIR protein.

Where the vesicles are prepared from *E. coli, Shigella* or *Salmonella* the bacterium may express no more than 4 of ToIA, ToIB, ToIQ, ToIR and PaI proteins. Thus at least one protein from the natural five-protein Tol-PaI system may be absent, resulting in a bacterium which, during growth in culture medium, releases greater quantities of outer membrane vesicles into the medium than the same bacterium expressing all 5 Tol-PaI proteins. Preferably ToIR is not expressed, but the other four proteins may be expressed (i.e. a ΔToIR strain).

In preferred embodiments, at least one of the five Tol-PaI proteins in *E. coli, Shigella* or *Salmonella* is removed e.g. by deletion or inactivation of the gene encoding the protein. Thus the bacterium may express 0, 1, 2, 3 or 4 of ToIA, ToIB, ToIQ, ToIR and PaI proteins. Removal of one of the five proteins can suffice, in which case the bacterium expresses only 4 of these proteins. Preferably the ToIR protein is removed e.g. by inactivation of a starting strain's toIR gene. Thus a preferred bacterium may be toIA+toIB+toIQ+ToIR-PaI+.

In some embodiments, the bacterium expresses all five Tol-PaI proteins, but at least one is mutated to cause hyperblebbing. For instance, the ToIA, ToIQ, ToIR and/or PaI protein may be mutated such that the protein retains its membrane localisation but its interactions with other members of the Tol-PaI system are disrupted. The bacterium will thus retain ToIA, ToIQ and ToIR as transmembrane proteins in the inner membrane, and PaI protein as a periplasm-facing lipoprotein in the outer membrane, but at least one of the ToIA, ToIQ, ToIR and/or PaI proteins is mutated and not fully functional.

In addition other mutations may also be present e.g. to give OAg-deficient strains, for instance in those cases where the —OAg functionality is not intended for desired immune response, or in those cases where the —OAg may negatively impact the immunogenicity against the heterologous antigen. In this direction, possible mutations may be ΔgaIU, ΔgaIE or ΔwbaP in *E. coli, Shigella* or *Salmonella* strains.

In one further preferred embodiment, a meningococcus does not express a functional MItA protein. Knockout of MItA (the membrane-bound lytic transglycosylase, also known as GNA33) in meningococcus provides bacteria which spontaneously release large amounts of nOMVs into culture medium, from which they can be readily purified. For instance, the vesicles can be purified using the two stage size filtration process, comprising: (i) a first filtration step in which vesicles are separated from the bacteria based on their different sizes, with the vesicles passing into the filtrate; and (ii) a second filtration step in which the vesicles are retained in the retentate.

In the present invention, it is preferred that —OAg is present on the nOMVs because we observed (e.g. nOMVs from *Salmonella* and *Shigella*) that, the presence of the —OAg on the surface of said nOMVs is advantageous in providing a bivalent vaccine, as the —OAg can act as a protective antigen. Some preferred strains have penta- or tetra-acylated less toxic LPS, which includes attached —OAg, after the mutation of msbB, htrB, ddg and/or PagP (see e.g. Rossi O et al, Clin Vaccine Immunol. 2016 Apr. 4; 23(4):304-14 and Rossi O et al, J Biol Chem. 2014 Sep. 5; 289(36):24922-35.

In *Neisseria*, the strain has preferably a modified fur gene. According to this embodiment, mutant *Neisseria* are engineered to reduce or switch off expression of at least one gene involved in rendering toxic the lipid A portion of LPS, in particular of IpxI1 gene. In this way, the resulting nOMVs present a reduced toxicity respect to the wild type strain, since the conversion of acylated lipid A in a less acylated form.

Similarly, preferred mutant *Neisseria* for the invention are engineered to reduce or switch off expression of at least one gene involved in the capsular saccharide synthesis or export, in particular of synX and/or ctrA genes. In this way, the resulting nOMVs may present a cross protection versus different serotypes, particularly appreciated by the skilled in the art.

In preferred embodiments a strain may include one or more of the knockout and/or hyper-expression mutations disclosed e.g. in Fukusawa et al. (1999), Vaccine 17:2951-2958. For instance, following the therein guidance and nomenclature, useful genes for down-regulation and/or knockout include: (a) Cps, CtrA, CtrB, CtrC, CtrD, FrpB, GaIE, HtrB/MsbB, LbpA, LbpB, LpxK, Opa, Opc, PiIC, PorB, SiaA, SiaB, SiaC, SiaD, TbpA, and/or TbpB; (b) CtrA, CtrB, CtrC, CtrD, FrpB, GaIE, HtrB/MsbB, LbpA, LbpB, LpxK, Opa, Opc, PhoP, PiIC, PmrE, PmrF, SiaA, SiaB, SiaC, SiaD, TbpA, and/or TbpB; (c) ExbB, ExbD, rmpM, CtrA, CtrB, CtrD, GaIE, LbpA, LpbB, Opa, Opc, PiIC, PorB, SiaA, SiaB, SiaC, SiaD, TbpA, and/or TbpB; or (d) CtrA, CtrB, CtrD, FrpB, OpA, OpC, PiIC, PorB, SiaD, SynA, SynB, SynX and/or SynC.

As above mentioned, the present conjugates are obtained by connecting at least one nOMV surface saccharide moiety (preferably comprised in the related —OAg) to one or more foreign selected antigen, i.e. that does not form part of the vesicle.

As far as the nOMV saccharide moiety is concerned, it has to be noted that it can be part of the —OAg functionality naturally present on the surface of the nOMV (e.g. in LPS or LOS), or it can be present within a different nOMV surface portion, e.g. a CPS, as herein below described in details. Advantageously, any proper antigen may be conjugated to the nOMV to obtain the nOMV-antigen conjugates of the invention, preferably in the form of a (poly)saccharide or polypeptide. In any case, the connection of one or more selected antigen produces an immunogenic conjugate which can raise an immune response which recognises said antigen, and which also recognises one or more components in the nOMV, thereby conveniently useful for the preparation of a multivalent vaccine. Antigens will be included in the present conjugates at a concentration which is high enough to elicit, when administered to a host, an immune response which recognises that antigen. Moreover, the immune response is preferably protective against the pathogen from which the antigen was derived, even more preferably against one of the pathogens listed below.

In one embodiment of the invention, the nOMV is conjugated to at least one homologous antigen, i.e. derived from the same organism from which the nOMVs are derived. In a still preferred embodiment, the selected antigen is a heterologous antigen i.e. derived from a different organism from the organism from which the nOMVs are derived.

In any case, the antigens are generally selected from any immunogenic polypeptides, i.e. polypeptides able to elicit an immune response when administered to a subject. Polypeptides used with the invention will include an amino acid having a residue, or a side chain, with a functional group suitable for conjugation, preferably an amino or a thiol group, even more preferably of general formula: —NH$_2$ or —SH. These residues may naturally be present in an antigen, or they may be introduced artificially for the purposes of conjugation. Preferred amino acid residues include, but are not limited to: arginine, lysine, asparagine, glutamine, cysteine and histidine. The most preferred amino acid residue for conjugation is lysine. Its —NH$_2$ side chain in fact can react with an activated oxidised —OH from a nOMV saccharide moiety and react with the thus obtained aldehyde group by reductive amination, according to the process as herein disclosed in details.

Polypeptide antigens are preferably prepared in substantially pure or substantially isolated form (i.e. substantially free from other polypeptides). They can be prepared by various means e.g. by chemical synthesis (at least in part), by digesting longer polypeptides using proteases, by translation from RNA, by purification from cell culture (e.g. from recombinant expression or from native culture), and the like. Recombinant expression in an *E. coli* host is a useful expression route. Polypeptide antigens can take various forms (e.g. native, fusions, glycosylated, non-glycosylated, lipidated, disulfide bridges and the like).

Polypeptide antigens used with the invention have a preferred average molecular weight of at least 1 kDa, more preferably of at least 3.5 kDa, even more preferably from 10 to 80 kDa. Still more preferably, the average molecular weight is comprised from 15 to 75 kDa.

Further preferred polypeptide antigens for conjugation to nOMVs according to the present invention comprise an epitope from a fungal, bacterial, protozoan or viral polypeptide. Preferred protozoan polypeptides are from a *Plasmodium* (such as *P. falciparum, P. vivax, P. ovale*). Particularly preferred bacterial polypeptides are selected from: *E. coli, N. meningitidis*, and Streptococci (such as *S. agalactiae, S. pneumoniae, S. pyogenes*).

Preferred *E. coli* polypeptide antigens include CTF1232, 405 and 3526. As a non-limiting preferred example, nOMV from *Shigella* or *Salmonella* can be conjugated to CTF1232, according to the present invention, to generate a bivalent vaccine covering both enterotoxigenic *E. coli* (ETEC) and *Shigella/Salmonella*.

In one embodiment, the considered *N. meningitidis* polypeptides are able, when administered to a mammal, to elicit an antibody response that is bactericidal against meningococcus. Preferred *N. meningitidis* polypeptides for use with the invention are selected from at least one of: NHBA, NadA, NsPA, NhhA, App and fHbp, as herein below detailed.

NHBA Antigen.

The NHBA antigen was included in the published genome sequence for meningococcal serogroup B strain MC58 as gene NMB2132 (GenBank accession number GI:7227388; SEQ ID NO: 2 herein). The sequences of NHBA antigen from many strains have been published since then. Various immunogenic fragments of the NHBA antigen have also been reported. Preferred NHBA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 2. The most useful NHBA antigens of the invention can elicit antibodies which, after administration to a subject, can bind to a meningococcal polypeptide consisting of amino acid sequence SEQ ID NO: 2. Advantageous NHBA antigens for use with the invention can elicit bactericidal anti-meningococcal antibodies after administration to a subject.

The NadA antigen was included in the published genome sequence for meningococcal serogroup B strain MC58 (see e.g. Tettelin et al. (2000) Science 287:1809-1815) as gene NMB1994 (GenBank accession number GI:7227256; SEQ ID NO: 3 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 3. The most preferred NadA antigens of the invention can elicit antibodies which, after administration to a subject, can bind to a meningococcal polypeptide consisting of amino acid sequence SEQ ID NO: 3. Advantageous NadA antigens for use with the invention can elicit bactericidal anti-meningococcal antibodies after administration to a subject. SEQ ID NO: 7 is one such fragment.

NspA Antigen.

The NspA antigen was included in the published genome sequence for meningococcal serogroup B strain MC58 (see e.g. Tettelin et al. (2000) Science 287:1809-1815) as gene NMB0663 (GenBank accession number GI:7225888; SEQ ID NO: 4 herein). The sequences of NspA antigen from many strains have been published since then. Various immunogenic fragments of NspA have also been reported. Preferred NspA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 4. The most preferred NspA antigens of the invention can elicit antibodies which, after administration to a subject, can bind to a meningococcal polypeptide consisting of amino acid sequence SEQ ID NO: 4. Advantageous NspA antigens for use with the invention can elicit bactericidal anti-meningococcal antibodies after administration to a subject.

NhhA Antigen.

The NhhA antigen was included in the published genome sequence for meningococcal serogroup B strain MC58 (see e.g. Tettelin et al. (2000) Science 287:1809-1815) as gene NMB0992 (GenBank accession number GI:7226232; SEQ ID NO: 5 herein). The sequences of NhhA antigen from many strains have been published since e.g. WO00/66741 and WO01/55182, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 5. The most preferred NhhA antigens of the invention can elicit antibodies which, after administration to a subject, can bind to a meningococcal polypeptide consisting of amino acid sequence SEQ ID NO: 5. Advantageous NhhA antigens for use with the invention can elicit bactericidal anti-meningococcal antibodies after administration to a subject.

App Antigen.

The App antigen was included in the published genome sequence for meningococcal serogroup B strain MC58 (see e.g. Tettelin et al. (2000) Science 287:1809-1815) as gene NMB1985 (GenBank accession number GI:7227246; SEQ ID NO: 6 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most preferred App antigens of the invention can elicit antibodies which, after administration to a subject, can bind to a meningococcal polypeptide consisting of amino acid sequence SEQ ID NO: 6. Advantageous App antigens for use with the invention can elicit bactericidal anti-meningococcal antibodies after administration to a subject.

fHbp Antigen.

The factor H binding protein exists as three variants (v1, v2 and v3), and the invention can use any of these as preferred embodiment.

A v1 fHbp preferably comprises (a) an amino acid sequence which has at least k' % identity to SEQ ID NO: 8, and/or (b) a fragment of SEQ ID NO: 8. k' refers to percentage identity and could be defined as any number from 1 to 100. With reference to amino acid or nucleic acid sequences, generally the identity used in the application starts from as low as 40% with specific references to higher percentages, i.e. 70%, 75%, 80%, etc.

The fragment will preferably include at least one epitope from SEQ ID NO: 8. Preferably, the v1 fHbp can elicit antibodies which are bactericidal against v1 strains e.g. against strain MC58 (available from the ATCC as 'BAA-335').

A v2 fHbp preferably comprises (a) an amino acid sequence which has at least k' % identity to SEQ ID NO: 1, and/or (b) a fragment of SEQ ID NO: 1. Information about 'k' and fragments are given above. The fragment will preferably include at least one epitope from SEQ ID NO: 1. Preferably, the v2 fHbp can elicit antibodies which are bactericidal against v2 strains e.g. against strain M2091 (ATCC 13091).

A v3 fHbp preferably comprise (a) an amino acid sequence which has at least k' % identity to SEQ ID NO: 9, and/or (b) a fragment of SEQ ID NO: 9. Information about 'k' and fragments are given above. The fragment will preferably include at least one epitope from SEQ ID NO: 9. Preferably, the v3 fHbp can elicit antibodies which are bactericidal against v3 strains e.g. against strain M01-240355.

Antigens from Group A *Streptococcus* (GAS), Group B *Streptococcus* (GBS) and Pneumococcus are also equally preferred. As non-limiting examples, GAS25 (Slo), GAS40 (SpyAD) and GAS57 (SpyCEP) antigens can be incorporated into conjugates in accordance with some embodiments of the invention.

*Plasmodium* antigens are further preferred. These can be from any suitable species, where preferred species are selected from: *P. falciparum, P. vivax* and *P. ovale*.

Still another preferred antigen is Pfs25 (SEQ ID NO: 10), which is a sexual stage antigen of *P. falciparum* expressed on the surface of zygote and ookinete forms of the parasite. Another preferred antigen is Pfs48/45, which is a transmission-blocking vaccine candidate. Recently the C-terminal 10 cysteine fragment (10C) of Pfs48/45, containing three known epitopes for transmission blocking antibodies, has been produced as a chimera with the N-terminal portion of GLURP (RO), the asexual blood-stage antigen glutamate-rich protein. The resulting fusion protein (RO10C) elicited high levels of transmission-blocking antibodies in rodents (see Theisen et al. (2014) Vaccine 32:2623-2630). Shing et al. (2015) Vaccine 33:1981-1986 describes a chimera containing truncated 6C-fragments, which increases the yield of correctly-folded conformer. The RO6C construct was able to elicit high titer transmission blocking antibodies in rats. RO6C (SEQ ID NO: 11) is a preferred antigen that can be conjugated according to the present invention.

Another preferred antigen is the circumsporozoite protein (CSP; SEQ ID NO: 12).

Shorter peptides from CSP may also be conjugated according to the present invention. For example, the 12 amino acid (NANP)$_3$ peptide (SEQ ID NO: 13) derived from CSP can be used according to preferred embodiments.

In another still preferred embodiment the antigens are a saccharide species. The invention is in fact also suitable for conjugating one or more selected saccharide antigens to nOMVs, whereby saccharides may be used in their full-length natural form. As an alternative, a particular size fraction can also advantageously be selected. Thus, the saccharides may be fragmented from their natural length, and optionally a size fraction of these fragments can be used. Even further, the saccharides are not limited to saccharides purified from natural sources and synthetic or semi-synthetic saccharides can be used instead.

Preferred saccharide antigens are bacterial capsular saccharides (CPSs). These include, but are not limited to, the capsular saccharides selected from at least one of: *Haemophilus influenzae* type B; *Neisseria meningitidis* serogroups A, C, W135, X and Y; *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F; *Salmonella* including *Salmonella enterica* serovar Typhi Vi, either full length or fragmented (indicated as Ni); *Streptococcus agalactiae* serotypes Ia, Ib, and III; *Streptococcus pyogenes*, *Shigella* sp, group A and B *Streptococcus* (GAS and GBS respectively). More preferred saccharide antigens are from *Neisseria meningitidis* serogroups A and C. Thus, according to an embodiment of the invention, the nOMV is a GMMA derived from MenB, and the selected antigen is a capsular saccharide from MenA or MenC. In a still additional embodiment, the invention refers to a GMMA from MenB conjugated to a capsular saccharide from MenA antigen via a polysaccharide residue, wherein said GMMA is also conjugated to a MenC antigen via a different polysaccharide residue, thus obtaining a double functionalized GMMA vesicle, as below described in more details.

In any case, and as above mentioned, the selected antigens could be conjugated to nOMVs derived from the same or even from a different bacterial strain, thus providing a multivalent conjugate. In this respect, in a more preferred embodiment of the invention, the nOMV and the saccharide antigen are derived from different bacterial strains.

Other preferred saccharide antigens are β-glucans, particularly useful for protecting against *C. albicans* (for a general reference see Sandlin et al. (1995) Infect. Immun., 63:229-37).

Other preferred saccharide antigens are poly-rhamnose oligosaccharides for protecting against Group A *Streptococcus* (GAS). Native GAS saccharide has a poly-rhamnose backbone substituted with NAcGlcN. Synthetic oligosaccharides of poly-rhamnose, or oligomers with the structure of native GAS saccharide, can be conjugated to nOMVs according to the invention.

According to a preferred embodiment, the nOMV conjugates of the invention comprise a nOMV surface saccharide moiety directly connected to a selected antigen, where the direct connection may be achieved by activation of the saccharide moiety followed by direct reaction (e.g. via reductive amination) with the selected antigen, as exemplified in the present Example 4. In an equally preferred embodiment, the nOMV is connected to the selected antigen indirectly, i.e. via a linker moiety, as herein described in more details and as exemplified in Example 3.

The conjugates of the invention are immunogenic, as demonstrated by the studies in mice and supported by the herein included experimental part. Advantageously, besides being capable of inducing an immune response against the conjugated antigen, the conjugates of the invention are also capable of inducing an immune response against the nOMV component, thus being good candidates for the preparation of multivalent immunogenic composition thereof. In fact, it has surprisingly been observed that conjugation of the selected antigens through the saccharide moiety present on the surface of the nOMV does not negatively impact the ability of the nOMVs to induce their own immune response, differently from dOMV. Accordingly, the conjugates of the invention may be useful e.g. as bi-valent immunogenic agent, suitable for preparing vaccines, with the nOMV and the conjugated heterologous antigen both showing good immunogenicity. Also, it has advantageously found that the conjugates of the invention induce high anti-antigen specific IgG response in mice, with no impact on anti —OAg IgG response, as supported for instance in the present Example 5 and 6. Conjugates of the invention offer further several advantages compared to unconjugated antigens, as for example set forth in Examples 3 to 6.

As formerly set forth, in a further aspect, the invention refers to a process for preparing the above described conjugates, comprising a first step of activating a nOMV-surface saccharide moiety, and a second step of connection of the thus obtained activated vesicle to at least one selected antigen, optionally via a divalent linker.

According to the present process, at least one saccharide moiety on a nOMV is conjugated to one selected antigen (as above described) to form a conjugate of the invention. According to a different embodiment, two or more saccharide moieties are conjugated to two or more different selected antigens, thus providing a nOMV derivative conjugated with two or more different antigens, particularly suitable for the preparation of polyvalent immunogenic compositions. As above indicated, the connection step typically involve activating the nOMV-surface saccharide moiety and/or the selected antigen. Similarly, the connection step may involve introducing a linker between the nOMV-saccharide moiety and the selected antigen, as below detailed. Thus, in one embodiment, the process of the invention comprises the steps of: (i) activating a saccharide moiety on the nOMV surface; and (ii) direct connection of the activated moiety with a selected antigen, to obtain the nOMV conjugates of the invention.

As an alternative embodiment, the process of the invention comprises the steps of: (i) activating a saccharide moiety on the nOMV surface; (ii) connecting the activated moiety to a divalent linker group to form a vesicle-linker conjugate; and (iii) connecting a selected antigen to the vesicle-linker conjugate to form the nOMV conjugates of the invention.

As another alternative embodiment, the process of the invention comprises the steps of: (i) activating a saccharide moiety on the nOMV surface; (ii) connecting a selected antigen to a divalent linker group to form an antigen-linker conjugate; and (iii) connecting the activated moiety of step (i) to the antigen-linker conjugate to form the nOMV conjugates of the invention.

As another alternative embodiment, the process of the invention comprises the steps of: (i) activating a saccharide moiety on the nOMV surface; (ii) connecting the activated moiety to a divalent linker group to form a vesicle-linker conjugate; (iii) connecting a selected antigen to a divalent linker group to form an antigen-linker conjugate; and (iv) connecting the linker moiety of step (ii) to the antigen-linker conjugate of step (iv) to form the nOMV conjugates of the invention.

As far as the nOMV saccharide moiety is concerned, it has to be noted that it can be part of the —OAg functionality, or of the core region naturally present on the surface of the nOMV (e.g. in LPS or LOS), or it can be present within a different nOMV surface portions, e.g. a CPS. In all these preferred cases, the process of the invention allows the connection of said saccharide moiety with a selected antigen in a simple and effective way, thus leading to the final nOMV conjugates of the invention, endowed with remarkable immunogenic activity. Advantageously, the presence of the —OAg does not substantially interfere with the response against the selected antigen. Comparative examples 9a-c show that when the present process is applied to dOMV, no conjugation with the antigen occurs, thus preventing the formation of the desired vesicle-antigen conjugate.

Depending on the species from which nOMVs are prepared, various saccharide moieties (including tetraose, pentose and hexose sugars) can be used for activation and subsequent conjugation. Preferably, lipopolysaccharides, via the —OAg portion or core region, or capsular saccharides may be used for activation and subsequent conjugation. Preferred saccharide moieties are selected from at least one of glucose, galactose, fructose, mannose, ribose, abequose, galactosamine, glucosamine, mannosamine, sialic acid, sulfoquinovose, erythrose, threose, arabinose, rhamnose, sorbose, ribuiose, xylose, xylulose, lyxose, tagatose or ketodeoxyoctulosonate. A saccharide moiety on the nOMV is preferably activated by oxidizing a hydroxyl group of the saccharide to form a carbonyl aldehyde functionality, in the presence of a suitable oxidizing agent, such as TEMPO or a periodated salt. This latter is preferably selected from an alkali periodate or a metaperiodate, more preferably $NaIO_4$. The oxidizing agent is preferably used as aqueous solution in a concentration ranging from 0.5 mM to 20 mM, preferably from 3 mM to 20 mM, where concentrations from 10 to 20 mM and from 0.5 to 5 mM or from 3 to 5 mM are still more preferred. Other activation reactions according to some embodiments occurs in the presence of cyanylating reagents such as CDAP (e.g. 1-cyano-4-dimethylamino pyridinium tetrafluoroborate), carbodiimides, hydrazides, active esters, norborane, p-nitrobenzoic acid, N-hydroxysuccinimide, S-NHS, EDC and TSTU.

In general, where polysaccharides are oxidised it is not necessary to oxidise all of the available sugars. Indeed, it can be desirable to retain at least part of the natural sugar structures, particularly where these are a useful antigen. Also to be noted is the fact that due to the peculiar nOMVs composition and conformation as above detailed, the polysaccharide moiety can be conveniently activated by the present process leading to the formation of a highly reactive oxidized nOMVs intermediate species. In a preferred embodiment, for a given saccharide moiety of interest, the proportion of oxidised residues can range from 1% to 100%, preferably from 10-50%, or from 20-40%, or from 20-35%, whereas oxidation of 20-35% within an —OAg structure is particularly preferred. In this direction, it has been found that said ranges allow for efficient conjugation with minor or substantially assent impact on the —OAg structural integrity. Also, it has been noticed that higher nOMV oxidation degree corresponds to lower —OAg size, meaning that there is major impact on native —OAg structure and its ability to induce a specific immune response. The proportion of oxidised residues can be determined by high-performance anion exchange chromatography with pulsed amperometric detection (HPAEC-PAD), by comparing the intact sugar residues pre- and post-oxidation. In this direction, it was found that the concentration of the oxidising agent and of the nOMV, along with the pH may influence the overall conduct of the oxidation step, as for instance indicated in the present Example 2, Table 2c. Thus, in a preferred embodiment, the oxidation agent is used in excess over the starting nOMV, where a molar excess of 3:1 or 2:1 respect to the number of monosaccharides that can be subjected to oxidation is particularly preferred. The oxidizing agent is preferably used as aqueous solution in a concentration ranging from 0.5 mM to 20 mM, preferably from 3 mM to 20 mM, where concentrations from 10 to 20 mM and from 0.5 to 5 or from 3 to 5 mM are still more preferred.

The concentration of nOMV is preferably comprised between 0.2 and 5 mg/mL.

Preferably, the pH is comprised between 4 and 8, whereas value from 5 and 7 are particularly preferred. To this extent, the pH may be adjusted using a buffer agent, such as acetate/phosphate and the like.

Said parameters can be conveniently set in order to have a preferred degree of oxidation comprised between 20% and 35% over the subjected saccharide moiety. This allows having an efficient further conjugation with the selected antigen, without substantially impacting the saccharide moiety structure.

For instance, Rha residues in an —OAg functionality can be oxidised as e.g. indicated in the below Scheme 2 using $NaIO_4$.

Scheme 2

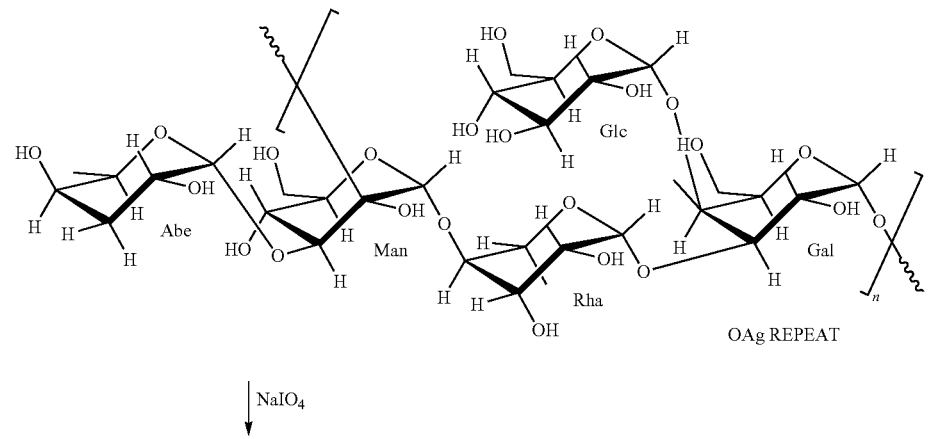

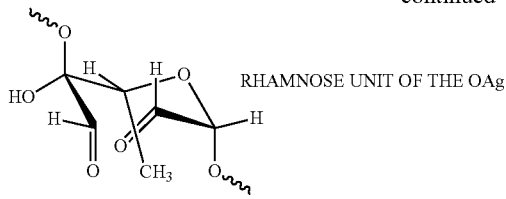
RHAMNOSE UNIT OF THE OAg

The oxidation step is typically performed at room temperature (e.g. from about 15° C. to about 40° C.), for a suitable time, e.g. comprised from 30 min to 3 h, depending for example on the amount and type of considered nOMV. In any case, it has been found that no substantial nOMV crosslink and/or aggregation occurred. This is of upmost importance also for the effectiveness of the subsequent conjugation step with the selected antigen as herein described in details.

After oxidation, nOMVs can optionally be subjected to a reduction step, for example with NaBH$_4$, to stabilise the oxidised nOMV by removing the formed CHO groups. The stabilised oxidised nOMV may then be stored and/or further characterised.

Typically, after the activation step of the present process, the obtained oxidized nOMVs are isolated and purified e.g. by ultracentrifugation at 4° C. at 110000 rpm for 30 min, and subsequently reacted with the selected antigen.

Thus in a preferred embodiment, the process comprises the steps of:
  (i) activation of the saccharide moiety on the nOMV surface, preferably by oxidation;
  (i-bis) isolation of the thus obtained oxidised nOMV; and
  (ii) connection of the oxidised nOMV of step (ii) with at least a selected antigen, optionally via a divalent linker.

In a still preferred embodiment, the process is performed in the presence of an alkaline sulphite, preferably Na$_2$SO$_3$. This is particularly advantageous because by quenching the oxidation reaction with Na$_2$SO$_3$, it is possible to perform the process in one step, i.e. avoiding the isolation of the intermediate oxidised nOMV (step (i-bis) above), as exemplified in the Example 5. This allows saving time, thus obtaining the final conjugate in a simple and effective way. In practice, and according to an exemplified embodiment, after the activation step (i) the reaction is quenched with a proper amount of the alkaline sulphite, and let to react for a proper frame of time (generally comprised from 5 to 20 minutes) in order to neutralize the excess of the oxidizing agent. After that, the selected antigen is directly added to the mixture (i.e. without isolation of the oxidised nOMV), according to step (ii), thus obtaining the nOMV conjugates of the invention.

As an alternative, the carbonyl aldehyde group of the saccharide moiety obtained by the oxidation step can be further modified to form a proper functionality which can then be reacted with the selected antigen or with a linker as the case may be (in this case to give a vesicle-linker conjugate which can then be coupled to the selected antigen).

The selected antigen is typically added at 1:1 w/w ratio with respect to the used nOMV, at room temperature, for a proper frame of time, e.g. comprised from 2 hours to 24 hours. When the antigen is derivatised with a linker, the reaction is conveniently carried out using an excess of antigen over the nOMV, preferably a 2:1 or more preferably a 3:1 w/w ratio, as indicated for instance in the present Example 3.

In a particularly preferred embodiment, the process of the invention comprises the steps of: (i) oxidation of a saccharide moiety; and (ii) reaction of the oxidized moiety with an amino group on a selected antigen residue. Even more preferably, said selected antigen residue is an amino —NH$_2$ group on a lysine residue within a polypeptide selected antigen.

Preferably, coupling of the oxidized saccharide moiety of the nOMV with the amino group, preferably a free —NH$_2$ group, of the antigen is achieved by reductive amination, more preferably using NaBH$_3$CN, e.g. according to procedure known in the art. The NaBH$_3$CN is used in weight amounts (w/w) comprised from 3 to ⅓, preferably 1 to 1, over the oxidized nOMV. Practically, the NaBH$_3$CN can be added together with the selected antigen, directly to the oxidised nOMV intermediate product, as generally illustrated in Schemes 3 and 4 below, using, by way of example, a nOMV that is conjugated via an oxidized rhamnose unit to malaria membrane proteins Pfs25 or R06C, respectively.

Scheme 3

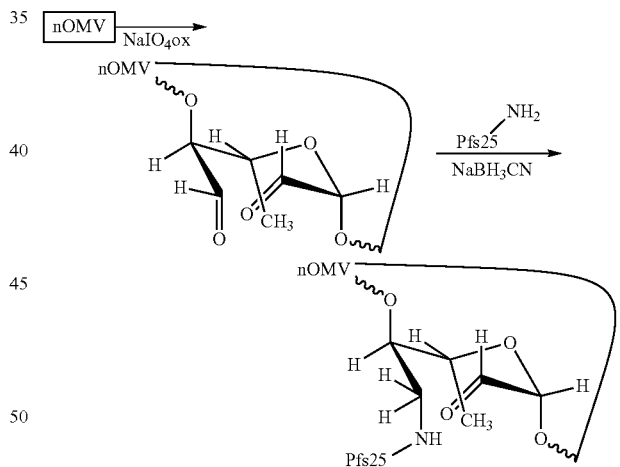

Scheme 4

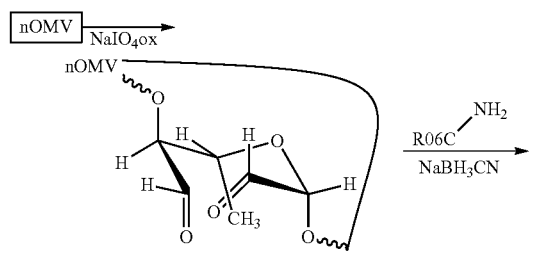

-continued

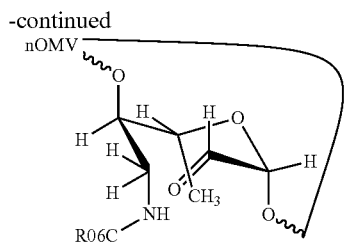

As an alternative embodiment, the selected antigen may be modified, either by introducing a linker group or by converting a functional group on the antigen into another functional group suitable for the reaction with the activated saccharide moiety on the nOMV, or with a linker of the vesicle-linker conjugate when used. In particular, if the selected antigen is a saccharide, it may be modified by reaction with a linker either randomly (r), meaning that the linker is introduced at multiple points along the sugar chain, or selectively (s), meaning that the linker is introduced at the reducing end of the sugar chain (i.e. at only one position). In a preferred embodiment, the linker is selective introduced at the terminal position of the selected antigen, as for instance indicated in the Example 3.

Selective modification of the antigen is preferably achieved by reaction with adipic acid dihydrazide (ADH) in the presence of NaBH$_3$CN, as generally shown in Scheme 5 using fVi as the antigen. Random modification of the antigen is preferably achieved by activation of one or more carboxylic acid groups on the antigen, for instance by using NHS/EDAC, and subsequent reaction with ADH, as shown in Scheme 6 using fVi as the antigen. This type of conjugation reaction is illustrated in Scheme 7 below, using, by way of example, a nOMV that is conjugated via an oxidized rhamnose unit to fVi modified to include a —NH$_2$ by reaction with ADH.

Scheme 5

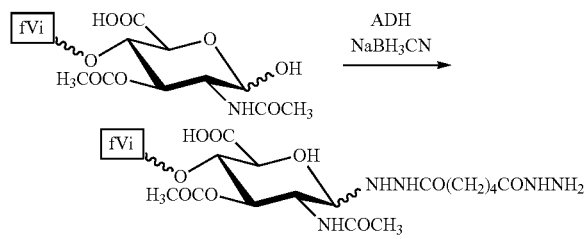

Scheme 6

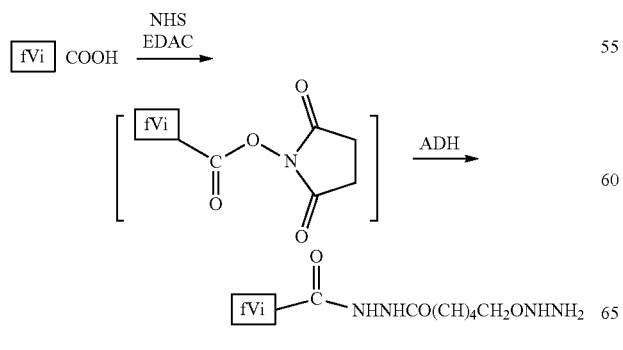

Scheme 7

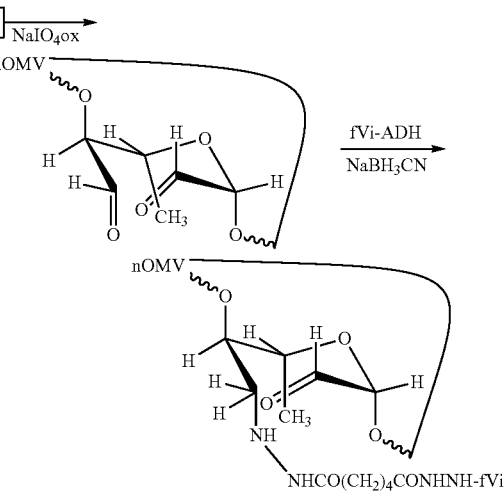

An alternative embodiment of the invention refers to a process comprising the steps of: a) modifying a selected antigen to include an amino group, preferably —NH$_2$; b) activating a nOMV by oxidising a hydroxyl group of a saccharide moiety as discussed above, and c) connecting the oxidized saccharide moiety to the modified antigen of step a), preferably, by reductive amination, as discussed above.

An alternative embodiment of the invention refers to a method of making a nOMV-antigen conjugate comprising connecting an oxidized saccharide moiety of an activated nOMV to a modified antigen, thereby making the nOMV conjugates of the invention, wherein the antigen was modified to include an amino group, preferably —NH$_2$, and wherein the nOMV was activated by oxidising a hydroxyl group of a saccharide moiety. In a further embodiment of the invention, the reacting step is reductive amination.

As above set forth in details, the nOMV conjugates of the invention comprise an activated nOMV surface saccharide moiety directly connected to a selected antigen.

In an equally preferred embodiment, the activated nOMV surface saccharide moiety is connected to the selected antigen indirectly, e.g. via a linker unit. This latter will generally be a bifunctional linker, using one functional group to react with the nOMV (via the activated saccharide moiety) and another functional group to react with the selected antigen. The linker can be a heterobifunctional linker or a homobifunctional linker of general formula (I):

$$X-L-X'  \quad (I)$$

wherein:
X and X' groups are independently the same or different as each other, and react with activated nOMV surface saccharide moiety and the selected antigen respectively; and
L is a linking spacer, preferably of general formula (II):

$$-L'-L2-L'- \quad (II)$$

wherein:
the two L' groups are independently the same or different as each other and are selected from: a carbonyl (C=O), ester (—C(O)O—) or amido group (—C(O)NR1-), wherein R1 is H or, a straight, or, when comprising at least 3 carbon atoms, a branched cyclic C1-C10 alkyl group having 1 to 10 carbon atoms (e.g. C1, C2, C3, C4, C5, C6, C7, C8, C9, C10); and L2 is a straight or branched C1-C10 alkyl group having 1 to 10 carbon atoms, preferably having C4 carbon atom, even more preferably in the form of a straight chain.

X group is preferably selected from: —NH$_2$, —NH—NH$_2$, —O—NH$_2$, optionally substituted sulfo-N-hydroxysuccinimide and N oxysuccinimide residue.

Where the reactions with both the nOMV and the selected antigen involve the same functional groups it is preferred to use a bifunctional linker of general formula (I), wherein both the two X groups are the same.

When the functional groups on the nOMV saccharide moiety and on the selected antigen are both aldehydes it is preferred to use a homofunctional linker having X selected from: —NH$_2$, —NH—NH$_2$ or —O—NH$_2$ reactive group. In a still preferred embodiment, the linker is the adipic acid dihydrazide (ADH) of general formula:

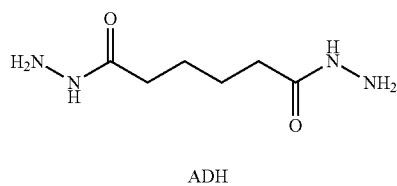

ADH

The linker may then be reacted with the nOMV and/or antigen by reductive amination as above set forth.

Preferred bifunctional linkers particularly useful for the reaction with amine groups of the selected antigen, are selected from: acryloyl halides, preferably chloride, disuccinimidyl glutarate, disuccinimidyl suberate and ethylene glycol bis[succinimidylsuccinate].

Other still preferred linkers are selected from: β-propionamido, nitrophenyl-ethylamine, haloacyl halides, glycosidic derivatives linkages, 6-aminocaproic acid.

In a still preferred embodiment, the linker is selected from: N-hydroxysuccinimide, N oxysuccinimide, even more preferably from adipic acid N-hydroxysuccinimide diester (SIDEA).

When the reaction with the nOMV and the antigen involves different functional groups (such as an amine on the nOMV and a thiol on the antigen,) it will be understood that a heterobifunctional linker will be used capable to selectively react with both the different functional groups. In this case, preferred heterobifunctional linkers are selected from at least one of: succinimidyl 3-(2-pyridyldithio)propionate (SPDP), succinimidyl 6-(3-[2-pyridyldithio]-propionamido) hexanoate (LC-SPDP), sulfosuccinimidyl 6-(3'-(2-pyridyldithio)propionamido)hexanoate (sulfo-LC-SPDP), 4-succinimidyloxycarbonyl-α-methyl-α-(2-pyridyldithio)toluene (SMPT), sulfosuccinimidyl-6-[α-methyl-α-(2-pyridyldithio)toluamideo]hexanoate (sulfo-LC-SMPT), succinimidyl 4-(N-maleimidomethyl)cyclohexane-1-carboxylate (SMCC), sulfosuccinimidyl 4-(N-maleimidomethyl)cyclohexane-1-carboxylate (suflo-SMCC), m-maleimidobenzoyl-N-hydroxysuccinimide ester (MBS), m-maleimidobenzoyl-N-hydroxysulfosuccinimide ester (sulfo-MBS), N-succinimidyl (4-iodoacetyl)aminobenzoate (STAB), sulfosuccinimidyl (4-iodoacetyl)aminobenzoate (sulfo-SIAB), succinimidyl 4-(N-maleimidophenyl)butyrate (SMPB), sulfosuccinimidyl 4-(N-maleimidophenyl)butyrate (sulfo-SMPB), N-γ-maleimidobutyryl-oxysuccinimide ester (GMBS), N-γ-maleimidobutyryl-oxysulfosuccinimide ester (sulfo-GMBS), succinimidyl-6-((((4-(iodoacetyl)amino) methyl)cyclohexane-1-carbonyl)amino)hexanoate (SI-ACX), succinimidyl 6-[6-(((iodoacetyl)amino)hexanoyl) amino]hexanoate (SIAXX), succinimidyl-4-(((iodoacetyl) amino)methylcyclohexane-1-carboxylate (SIAC), and succinimidyl 6-[(iodoacetyl)amino]hexanoate (SIAX) and p-nitrophenyl iodoacetate (NPIA).

In a further embodiment, the process encompasses the possibility to recycle the unreacted selected antigen particularly when in form of polypeptide. To this extent, it has been found that the unreacted antigen from the conjugation mixture can be conveniently recycled in the conjugation step, thus improving the overall efficiency of production of the conjugates of the invention, and obtaining final conjugates still endowed with remarkable immunogenicity (see present Example 6).

As above explained in details, the present process allows the preparation of the nOMV conjugates of the invention in a simple and convenient way, also requiring fewer steps when compared to previous methods for the preparation of similar conjugated derivatives (e.g. starting from dOMV). Thus the invention also refers to a nOMV conjugate obtained (or obtainable) by the process of the invention, according to the above described embodiments. Particularly, the present process does not necessarily require the expensive step of polypeptide antigen derivatisation, as well as not performing an extraction (e.g. using a detergent) or denaturation of the starting vesicles. Production and purification of nOMVs of the invention in fact is less expensive than for traditional carrier proteins and more robust and consistent than production of dOMV. nOMV used in the invention can be produced at high yields using e.g. two simple tangential flow filtration steps, and avoiding detergent extraction procedures. In addition, the unreacted selected antigen can be recycled from the conjugation mixture for use in the process, improving the efficiency of preparation of the conjugates, as exemplified in the Example 6. Also, the present invention offers an easy way to prepare a polyvalent vaccine i.e. a vaccine which includes multiple immunogens (typically from different pathogens) by property choosing the nOMV and the selected antigen as herein described in more details. In fact, due to its versatility, the present process may be conveniently and effectively applied to nOMV from different sources (e.g. *Salmonella, Shigella* and meningococcal), being applied with success to both protein and saccharide antigens. Finally, it has to be noted that the present process not only allows for the preparation of highly immunogenic conjugates, but also it does not substantially change the nOMV integrity and size distribution. This is particularly appreciated by the skilled in the art, because the absence of nOMV aggregates allows for a better yield and overall consistency and robustness of the present process.

The present invention is also useful for the preparation of variously functionalized nOMVs conjugates, allowing multivalent presentation of different antigens on the surface of the selected vesicle.

Thus, according to a preferred embodiment, the invention refers to a conjugate comprising a native outer membrane vesicle as above set forth, having at least a surface saccharide moiety connected to at least a first antigen, wherein said first antigen is connected to a second different antigen according to the general formula (I):

nOMV-Ag1-Ag2     (I)

In this direction, the two selected antigens (herein indicated as Ag1 and Ag2) may be coupled together to give an Antigen-Antigen derivative (Ag1-Ag2), which can be subsequently connected to the selected nOMV surface saccharide moiety via a reductive amination procedure as above described.

Alternatively, the nOMV surface saccharide can be first connected to the selected Ag1 via a reductive amination procedure as above described, to give a nOMV Ag1 conjugate, and subsequently a second Ag2 is connected to said nOMV-Ag1 conjugate, to give the conjugate of the above general formula (I).

In any case, preferred native outer membrane vesicles are the GMMA vesicles, more preferably from *Neisseria* MenB. The Ag1 and Ag2 can be selected among the preferred antigens as above described, being protein or polysaccharide moieties. Preferably, the antigens used for the multi functionalization as herein contemplated are both proteins or both polysaccharides, or even protein or saccharide.

In any case, the connection between the antigens and the nOMV saccharide moiety can be carried out directly, or by using activating agents, or suitable linkers according to the herein described preferred embodiment.

Thus according to a more preferred embodiment, the invention refers to a conjugate of the above general formula (I), wherein Ag1 comprises the (NANP)$_3$ protein antigen, Ag2 comprises the Pfs25 protein antigen, more preferably having the nOMV particle obtained from S. Typhimurium.

In more details, said conjugate is preferably prepared by a process comprising the steps of:
a) activating the Pfs25 antigen using EMCS, to give the below indicated activated Pfs25 intermediate:

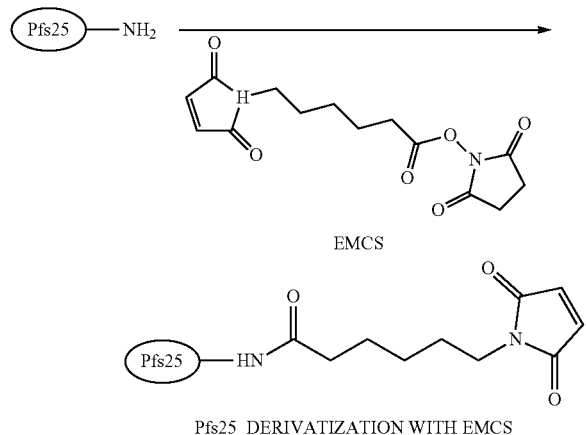

Pfs25 DERIVATIZATION WITH EMCS b) connecting said activated Pfs25 intermediate with (NANP)$_3$ to give the Pfs25-EMCS-(NANP)$_3$ derivative:

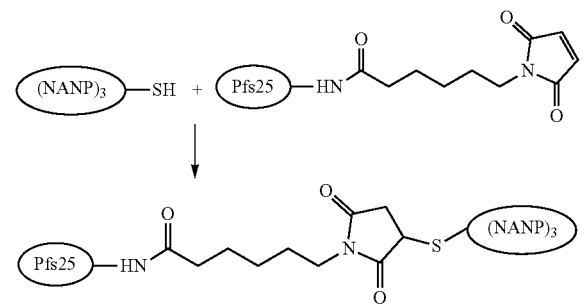

c) reacting the Pfs25 portion of such derivative with the native outer membrane vesicle intermediate, via reductive amination reaction according to the above described embodiments to give the GMMA Pfs25-(NANP)$_3$ conjugate.

Western blot analysis confirmed the formation of the conjugate where the Pfs25 is connected to the GMMA surface saccharide moiety, and no aggregation is detected.

According to a further embodiment, the present invention refers to an immunogenic conjugate comprising a native outer membrane vesicle, having at least a surface saccharide moiety connected to a first antigen (Ag1) via a reductive amination procedure as above described, and at least a surface saccharide moiety connected to a second different antigen (Ag2) via a reductive amination procedure as above described to give a conjugate indicated by the general formula (II):

Ag1-nOMV-Ag2 (II)

According to a preferred embodiment, in the above general formula (II), the nOMV is a GMMA from MenB, Ag1 is a capsular polysaccharide from meningococcal serogroup C, and Ag2 is a capsular polysaccharide from meningococcal serogroup C.

The conjugates of formula (II) can advantageously provide selective multi functionalization of nOMV, by using a specific functionalization pattern, by using the reductive amination procedure according to the invention. The skilled person will recognize that in light of the versatility of the proposed technology, the present invention may be suitably used for the multi functionalization of nOMV, preferably GMMA, even with more than 2 different antigens. Beside the possibility of selecting different antigens, the present invention also allows for the introduction of different amount of antigens, thus modulating the antigen/nOMV ratio according e.g. to the selected antigen or nOMV.

According to a further aspect, the invention refers to the above described nOMV-antigen conjugate for use as a medicament, particularly as immunogenic agent, even more preferably for one or more of the pathogens as herein indicated. In other words, the invention refers to the use of the present nOMV conjugates for the manufacture of an immunogenic composition.

According to a further aspect, the invention thus refers to an immunogenic composition, preferably a vaccine, comprising a conjugate of the invention and at least one additional pharmaceutically acceptable carrier, excipient or adjuvant. Generally, pharmaceutically acceptable carrier or excipient, can be any substance that does not itself induce the production of antibodies harmful to the patient receiving the composition, and which can be administered without undue toxicity. Pharmaceutically acceptable carriers and excipient are those used in the art, and can include liquids such as water, saline, glycerol and ethanol. Auxiliary substances, such as wetting or emulsifying agents, pH buffering substances, and the like, can also be present in such vehicles, according to the prior art.

The invention also provides a method for raising an immune response in a vertebrate, preferably a mammal, comprising administering a conjugate of the invention to the mammal or other vertebrate. The invention also provides conjugates of the invention for use in such methods. The immune response is preferably protective and preferably involves antibodies. The method may raise a booster response. The mammal is preferably a human. The subject in which disease is prevented may not be the same as the subject that receives the conjugate of the invention. For instance, a conjugate may be administered to a female (before or during pregnancy) in order to protect offspring (so-called 'maternal immunisation'). Conjugates of the invention may also be used to immunise other mammals e.g. cattle, sheep and pigs (especially against *Salmonella* sp.), and other non-mammal vertebrates including fish and poultry.

The invention provides conjugates for use in therapy (e.g. as immunogenic compositions or as vaccines). The invention also provides a conjugate for use in a method for raising an immune response in a vertebrate, preferably a mammal. The invention also provides the use of a conjugate in the manufacture of a medicament for raising an immune response in a vertebrate, preferably a mammal. The uses and methods are particularly useful for preventing/treating a variety of diseases, depending on the antigens and nOMVs within the conjugates as above set forth. Preferred conjugates of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Immunogenic compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration is preferred e.g. to the thigh or the upper arm. Injection may be via a needle (e.g. a hypodermic needle), but needle-free injection may alternatively be used. A typical intramuscular dose is about 0.5 ml. The invention may also be used to elicit systemic and/or mucosal immunity. Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Infections affect various areas of the body and so the compositions of the invention may be prepared in various forms. For example, the compositions may be prepared as injectable, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred. The composition is preferably sterile. It is preferably pyrogen-free. It is preferably buffered e.g. at between pH 6 and pH 8, generally around pH 7. Compositions of the invention may be isotonic with respect to humans. Immunogenic compositions comprise an immunologically effective amount of a conjugate of the invention, as well as any other of other specified components, as needed. Dosage treatment may be a single dose schedule or a multiple dose schedule (e.g. including booster doses). The composition may be administered in conjunction with other immunoregulatory agents.

Adjuvants which may be optionally used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed for instance in Watson, Pediatr. Infect. Dis. J. (2000) 19:331-332. The use of an aluminium hydroxide and/or aluminium phosphate adjuvant is particularly preferred. These salts include oxyhydroxides and hydroxyphosphates. The salts can take any suitable form (e.g. gel, crystalline, amorphous, etc.).

Conjugates of the invention which include nOMVs from one pathogen and a selected antigen from a second pathogen can be useful as multivalent vaccines. Pairs of pathogens which may be combined (one as antigen, and the other as a nOMV vesicle) include, but are not limited to: *N. meningitidis* and non-typhoidal *Salmonella* (e.g. *Salmonella Typhimurium* or *Salmonella Enteritidis*); *P. falciparum* and non-typhoidal *Salmonella*; *Salmonella Typhi* and non-typhoidal *Salmonella*; ETEC and *Shigella* sp.; Group A *Streptococcus* (GAS) and *N. meningitidis*; and GAS and non-typhoidal *Salmonella*.

Preferred pairings of the invention are indicated in the following Table A.

TABLE A preferred nOMV-Ag combinations

| nOMV | Antigen |
|---|---|
| Salmonella Typhimurium | Neisseria meningitidis fHbp |
| Salmonella Typhimurium | Plasmodium falciparum CSP |
| Salmonella Typhimurium | Plasmodium falciparum Pfs25 |
| Salmonella Typhimurium | Plasmodium falciparum RO6C |
| Salmonella Typhimurium | Plasmodium falciparum RO10C |
| Salmonella Typhimurium | Escherichia coli CTF1232 |
| Salmonella Typhimurium | S. Typhi Vi saccharide |
| Neisseria meningitidis | Neisseria meningitidis fHbp |
| Neisseria meningitidis | Poly-rhamnose oligosaccharide |
| Shigella, preferably sonnei | Escherichia coli CTF1232 |
| Neisseria meningitidis B | Capsular saccharide from MenA |
| Neisseria meningitidis B | Capsular saccharide from MenC |

Thus, the present nOMV-antigen conjugates are particularly useful as immunogenic agents against the pathogens listed in Table A.

Conjugates of the invention which include nOMVs from one pathogen and a selected antigen from a second pathogen can be useful as immunogenic compounds for the preparation of multivalent vaccines. Thus the invention provides a composition comprising a conjugate of the invention and one or more of the following further antigens:

a saccharide antigen from *N. meningitidis* serogroup A, C, W135 and/or Y,
a saccharide antigen from *Streptococcus pneumonia*,
an antigen from *hepatitis* A virus, such as inactivated virus,
an antigen from *hepatitis* B virus, such as the surface and/or core antigens,
a diphtheria antigen, such as a diphtheria toxoid e.g. the CRM197 mutant,
a *tetanus* antigen, such as a *tetanus* toxoid,
an antigen from *Bordetella pertussis*, such as pertussis holotoxin (PT) and filamentous haemagglutinin (FHA) from *B. pertussis*, optionally also in combination with pertactin and/or agglutinogens 2 and 3,
a saccharide antigen from *Haemophilus influenzae* A or B, polio antigen(s) such as IPV,
measles, mumps and/or *rubella* antigens,
influenza antigen(s), such as the haemagglutinin and/or neuraminidase surface proteins,
an antigen from *Moraxella catarrhalis*,
an protein antigen from *Streptococcus agalactiae* (group B *streptococcus*),
a saccharide antigen from *Streptococcus agalactiae* (group B *streptococcus*),
an antigen from *Streptococcus pyogenes* (group A *streptococcus*),
an antigen from *Staphylococcus aureus*.

The invention will be now described by the following experiment part, without posing any limitation to its scope.

EXPERIMENTAL PART

Example 1: nOMV Production

Preferred nOMVs used in the present experimental part are GMMA prepared from ΔtoIR strains of *S. Typhimurium* or *S. sonnei*, as e.g. disclosed in Clin Vaccine Immunol. 2016 April; 23(4): 304-314 and PLoS One. 2015; 10(8): e0134478 respectively.

Characteristics of said nOMVs were as indicated in the following Table 2.

TABLE 2 characteristics of purified nOMVs prepared from ΔtoIR strains of *S. Typhimurium* or *S. sonnei*.

| | S. Typhimurium 1418 (ΔtoIR) | S. sonnei 1790 (ΔtoIR ΔhtrB) |
|---|---|---|
| Diameter (nm) | 131.5 | 140 |
| Surface charge (mV) | −14.1 | −9.87 |
| Lipid A/mg vesicles | 172.8 | 155.4 |
| OAg/total protein weight ratio | 0.84 | 0.039 |

Example 2: nOMV Oxidation

A variety of oxidation conditions were tested. For example, for oxidation of nOMV ΔtoIR 1418, NaIO$_4$ concentrations in the range 5-20 mM were tested. The effect of oxidation on the —OAg chain length was assessed. Chain length was reduced as oxidation progressed. Higher NaIO$_4$ concentrations tended to reduce the OAg size. It was verified that increasing NaIO$_4$ molarity not only led to higher oxidation levels, from 5 to 45% (with rhamnose the main sugar involved in the process), but also reduced —OAg chain length. At the same time there was no change in vesicle size distribution, and integrity of the vesicles was maintained.

This was verified by dynamic light scattering (dls), nanoparticle tracking analysis (NTA) and high performance liquid size exclusion chromatography/multi-angle light scattering (HPLC-SEC/MALS; see Table 2a). It was also verified that NH$_2$ groups on nOMV did not react with produced CHO groups in conditions of reductive amination resulting in bigger cross-linked particles (Table 2b).

TABLE 2a analysis of oxidised nOMV (obtained by reaction with 10 and 20 mM NaIO$_4$) by dls and HPLC-SECMALS.

| Sample | Z-Average (PdI) (nm by dls) | Rw (nm by MALS) |
|---|---|---|
| 1418 ΔtoIR nOMV | 131.5 (0.219) | 30.5 |
| 1418 ΔtoIR nOMVox 10 mM | 129.5 (0.273) | 27.4 |
| 1418 ΔtoIR nOMVox 20 mM | 135.8 (0.224) | 30.5 |

TABLE 2b no reaction of nOMV under conditions of reductive amination verified by dls and HPLC-SEC/MALS.

| Sample | Z-Average (PdI) nm by dls | Rw nm by MALS |
|---|---|---|
| 1418 ΔtoIR nOMVox 20 mM NaIO$_4$ | 135.8 (0.224) | 30.5 |
| 1418 ΔtoIR nOMVox 20 mM NaIO$_4$ after reaction with NaBH$_3$CN | 131.7 (0.291) | 31.2 |

In conditions of reductive amination, without nOMV, the foreign antigen to conjugate does not give any aggregation, as verified for several antigens (e.g. fHbp, Pfs25 and CTF1232).

In addition, it was verified that NaBH$_3$CN does not reduce S—S bonds, which could otherwise affect conformation of proteins such as Pfs25. Pfs25 was treated with NaBH$_3$CN by mimic conjugation conditions, and the same reaction was performed with DTT as a reducing agent for comparison. After mixing overnight at room temperature, analysis by SDS PAGE and HPLC-SEC of Pfs25 treated with NaBH$_3$CN, in contrast to Pfs25 treated with DTT, showed no changes of the protein compared to fresh Pfs25. The same results were confirmed by MALDI-MS analysis, when the protein was treated with iodoacetamide (IAA) in the presence of NABH$_3$CN or DTT.

Further experiments on *S. Typhimurium* triple mutant nOMV (*S. Typhimurium* 2192 nOMV ΔtoIR ΔPagP ΔmsbB) showed that low NaIO$_4$ concentrations (3-5 mM) were also sufficient to obtain good oxidation levels. Exemplary results are shown in Table 2c, using nOMV concentration in the range 0.2-4 mg/mL, pH in the range 5-8, and NaIO$_4$ concentration in the range 0.5-5 mM. The resultant vesicles were assessed for % nOMV recovery, % rhamnose oxidation, nOMV size, and OAg size.

TABLE 2c

*S. Typhimurium* triple mutant nOMV oxidation.

| RUN | Factor 1<br>A: [nOMV]<br>μg/mL | Factor 2<br>B: [NaIO$_4$]<br>mM | Factor 3<br>C: pH | Response 1<br>% nOMV<br>recovery<br>(micro<br>BCA)<br>% | Response 2<br>% Rha<br>oxidation<br>(HPAEC-<br>PAD)<br>% | Response 3<br>nOMV<br>size (Z<br>average<br>r dls)<br>nm | Response 4<br>OAg size<br>(MP dRI)<br>kDa |
|---|---|---|---|---|---|---|---|
| 1 | 2100 | 2.75 | 6.5 | 72 | 10 | 50.28 | 20907 |
| 2 | 2100 | 2.75 | 8 | 75 | 6 | 50.77 | 24215 |
| 3 | 4000 | 0.5 | 5 | 79 | 0 | 51.52 | 31148 |
| 4 | 2100 | 2.75 | 5 | 80 | 13 | 48.09 | 17935 |
| 5 | 200 | 5 | 5 | 87 | 58 | 42.39 | 6826 |
| 6 | 2100 | 2.75 | 6.5 | 77 | 7 | 50.4 | 20276 |
| 8 | 4000 | 2.75 | 6.5 | 81 | 3 | 50.89 | 25221 |
| 9 | 2100 | 5 | 6.5 | 82 | 23 | 47.56 | 10170 |
| 10 | 2100 | 2.75 | 6.5 | 80 | 10 | 49.8 | 18493 |
| 11 | 2100 | 0.5 | 6.5 | 85 | 1 | 50.39 | 30592 |
| 12 | 200 | 0.5 | 5 | 83 | 7 | 50.19 | 25131 |
| 13 | 2100 | 2.75 | 6.5 | 82 | 9 | 50.85 | 18493 |
| 14 | 2100 | 2.75 | 6.5 | 78 | 10 | 49.07 | 20589 |
| 15 | 200 | 0.5 | 8 | 77 | 2 | 51.42 | 30347 |
| 16 | 200 | 5 | 8 | 72 | 20 | 47.69 | 10980 |
| 17 | 2100 | 2.75 | 6.5 | 83 | 8 | 49.09 | 20536 |
| 18 | 4000 | 5 | 8 | 80 | 11 | 48.44 | 18212 |
| 19 | 4000 | 0.5 | 8 | 78 | 1 | 50.86 | 30208 |
| 20 | 4000 | 5 | 5 | 86 | 15 | 48.6 | 16611 |

Similar rates of nOMV recovery were seen for all reaction conditions, as tested by micro bicinchoninic acid protein assay (micro BCA). It was further verified that none of the reaction conditions tested gave rise to nOMV crosslinking or aggregation.

The percentage rhamnose oxidation was affected by both nOMV concentration and NaIO$_4$ concentration, with lower nOMV concentration and higher NaIO$_4$ concentration tending to give higher rates of rhamnose oxidation. Accordingly, in general, the nOMV concentration and/or the NaIO$_4$ concentration can be manipulated to achieve the desired rate of rhamnose (or other sugar) oxidation.

To compare vesicles with different —OAg size and levels of rhamnose oxidation, the vesicles from runs 5, 14 and 16 of Table 5 were treated with NaBH$_4$ to remove aldehyde (CHO) groups and stabilise the nOMV vesicles, and the rhamnose oxidation level and —OAg size were assessed again after treatment. The results are shown below in Table 2d.

The results show that the reduction step did not affect —OAg length or the degree of nOMV oxidation. Similar results were obtained in a separate experiment.

Example 3: nOMV-Ag Conjugation Step (fVi—*S. Typhimurium* nOMV; Indirect Conjugation Via Linker fVi was modified by reaction with an ADH linker, either randomly (r) or selectively (s). The modified fVi was then conjugated to oxidised *S. Typhimurium* nOMV using reductive amination. When fVi was randomly activated with ADH, a fVi to nOMV 1:1 weight ratio was used in conjugation, while a 3:1 weight ratio was used when fVi was terminally derivatised with ADH. The conjugates were characterized using micro BCA/Lowry assay to determine the total protein content (nOMV recovery); high-performance anion-exchange chromatography pulsed amperometric detection (HPAEC-PAD) was used to determine total Vi TABLE 2d runs 5, 14 and 16 treatment with NaBH$_4$.

| Conditions<br>for oxidation | % Rha ox<br>expected | OAg size<br>expected | Pre reduction | | Post reduction | |
|---|---|---|---|---|---|---|
| | | | % Rha ox<br>obtained | OAg size<br>obtained | % Rha ox<br>obtained | OAg size<br>obtained |
| Run 5 | 58 | 6826 Da | 58 | 7481 Da | 53 | 6039 Da |
| Run 16 | 20 | 10980 Da | 14.4 | 18162 Da | 16 | 16528 Da |
| Run 14 | 10 | 20589 Da | 13 | 24224 Da | 12 | 21163 Da | content (no nOMV interference); high performance liquid chromatography size-exclusion chromatography (HPLC-SEC using a TSK gel 3000 PWxI column) was used to estimate the free Vi % using differential Refractive Index (dRI) and dynamic light scattering high performance liquid chromatography size-exclusion chromatography multi-angle static light scattering (DLS/HPLC-SEC MALS) was used to determine size. The effect of conjugation conditions of this conjugation method on the final number of fVi chains per nOMV was assessed considering the HPAEC-PAD collected data along with the number of nOMV by Nanoparticle Tracking Analysis (NTA).

The results are given in Table 3.

Example 3a: Vi-*S. Typhimurium* nOMV Conjugates (Indirect Conjugation Via Linker The conjugates 1 and 5 according to Table 3 above, having Vi:nOMV w/w ratios 0.45 and 0.44 respectively,) were tested in mice. For comparison, CRM197 was also used as a carrier, and simple mix of fVi+nOMV was also tested.

Mice were immunised subcutaneously at days 0 & 28 with the conjugates (1 µg Vi dose) and an Alhydrogel adjuvant. Anti-Vi IgG titers were measured at days 0, 14, 28

TABLE 3 influence of the NaIO$_4$ concentration and pH on fVi-nOMV conjugates.

| run | fVi avMW/kDa | r/s | % fVi RU activated (r)/% fVi chains activated (s) | [NaIO$_4$] for nOMV oxidation | pH of conjugation | nOMV recovery % | w/w ratio fVi/nOMV | chains fVi/particle nOMV |
|---|---|---|---|---|---|---|---|---|
| 1 | 48.5 | r | 24.4 | 20 | 4.5 | 30.7 | 0.45 | 97 |
| 2 | 48.5 | r | 24.4 | 20 | 6 | 43.8 | 0.35 | 76 |
| 3 | 48.5 | r | 30.4 | 20 | 7.2 | 58.8 | 0.2 | 43 |
| 4 | 48.5 | s | >95 | 10 | 7.2 | 69 | 0.08 | 17 |
| 5 | 48.5 | s | >95 | 20 | 4.5 | 48.9 | 0.44 | 95 |
| 6 | 48.5 | s | >95 | 10 | 4.5 | 80 | 0.43 | 93 |
| 7 | 23 | r | 11 | 20 | 4.5 | 80 | 0.08 | 37 |
| 8 | 23 | r | 11 | 10 | 4.5 | 89.4 | 0.07 | 32 |
| 9 | 23 | r | 11 | 10 | 6 | 77 | 0.04 | 18 |
| 10 | 8 | r | 23.8 | 10 | 4.5 | 100 | 0.12 | 158 |
| 11 | 3.8 | r | 15.5 | 20 | 4.5 | 100 | 0.05 | 138 |
| 12 | 3.8 | r | 15.5 | 10 | 4.5 | 67.6 | 0.07 | 194 |
| 13 | 3.8 | r | 15.5 | 10 | 6 | 82 | 0.02 | 55 |
| 14 | 3.8 | r | 16.2 | 10 | 7.2 | 74 | 0.01 | 30 | r: random linker (ADH) introduction along the fVi antigen.

s: selective linker (ADH) introduction at fVi antigen terminal end.

RU: repeating units.

aMW misured by HPLC-SEC by using dextran standards.

Performing reductive amination at pH 4.5 with 48.5 kDa Ni, resulted in higher fVi/nOMV ratios and more fVi chains per nOMV at both 10 mM and 20 mM of NaIO$_4$, than at higher pH. With randomly modified Ni, precipitation occurred at pH 4.5; precipitation was avoided by working with selectively modified Ni. In general, selective chemistry was identified as a way to improve nOMV recovery and avoid precipitation. Precipitation was not observed for fVi with an avMW ≤23 kDa at low pH with randomly modified fVi chains.

Oxidation of nOMV with 10 mM of NaIO$_4$ instead of 20 mM resulted in improved conjugate recovery. Increasing the concentration of NaIO$_4$ did not impact the characteristics of the final conjugates.

Figure 2A:
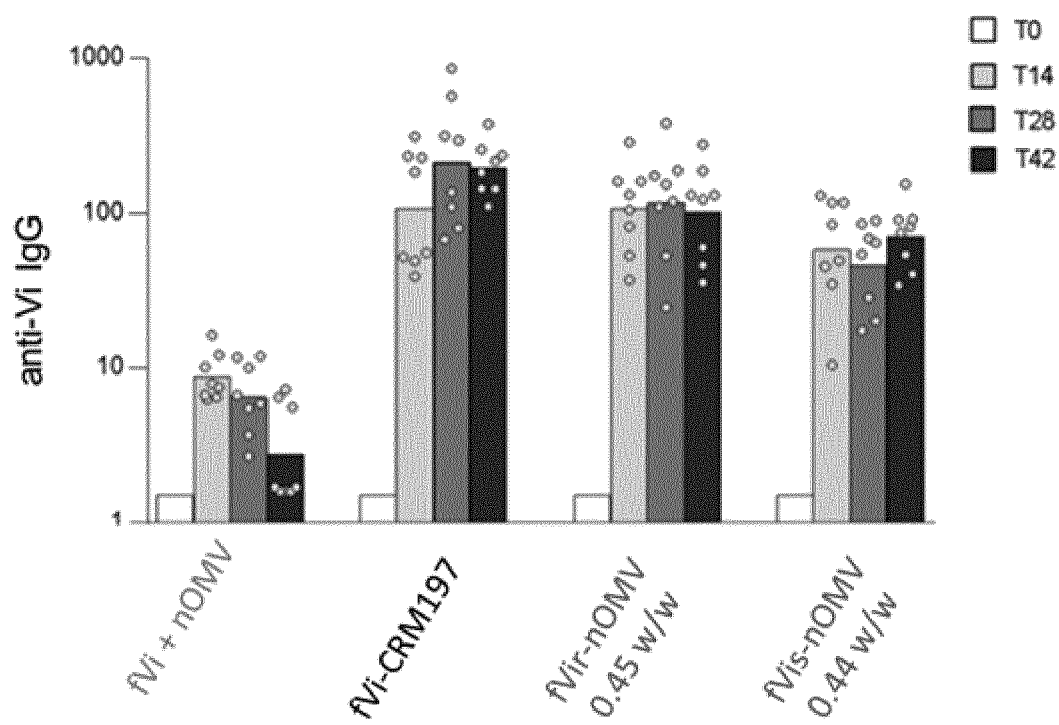
FIG. 2 show anti-Vi (FIG. 2A) and anti-OAg (FIG. 2B) IgG titers after immunisation with fragmented Vi (fVi) saccharide conjugated to *S. Typhimurium* nOMV compared to fVi physically mixed with said nOMV or conjugated to the more traditional carrier CRM197 (formulated with Alhydrogel). CD1 female mice, 5 weeks old (8 per group) were subcutaneously immunised at days 0 and 28 with 1 µg Vi/dose. Titres were measured at days 0, 14, 28 and 42.

When using 23 kDa Ni, lower fVi to nOMV ratios were obtained, which could be related to the lower derivatization percentage of M-ADH used for conjugation (11% of fVi repeating units). pH and activation degree of M-ADH were identified as variables for modulation of the number of fVi chains linked per nOMV.

and 42, and results are shown in FIG. 2A. nOMV was non-inferior to CRM197, but was significantly better than the unconjugated mixture.

Figure 2B:
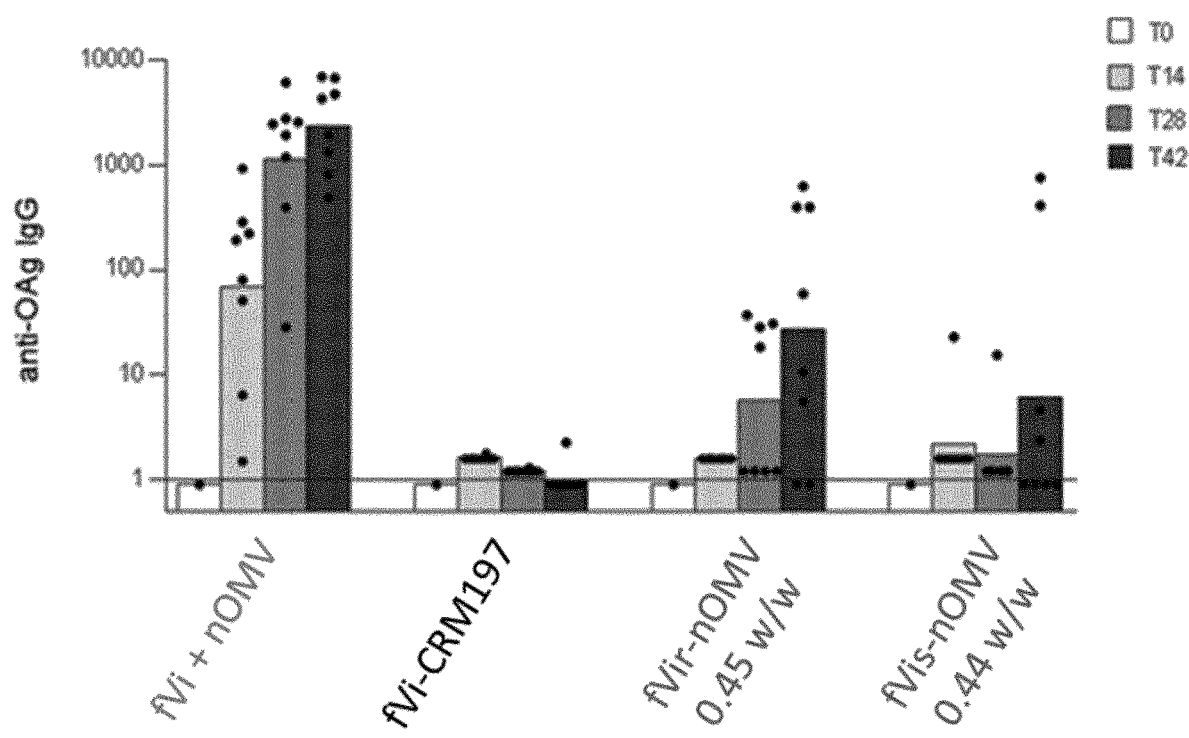

IgG titers against the —OAg were also assessed. FIG. 2B shows anti-OAg titers for the vesicle alone or conjugated to Vi. Conjugation reduced the —OAg response by a small amount, but responses remained significant.

Example 4: nOMV-Ag Conjugation Step (ETEC CTF1232—*S. Typhimurium* ΔtolR 1418 or *S. sonnei* 1790 nOMV; Direct Conjugation without Liker CTF1232 is an *E. coli* antigen (SEQ ID NO: 14 with a C-terminus hexa-histidine tag that was conjugated to the two types of nOMV vesicles. The polypeptide includes five lysine residues which can be used for linking to oxidised saccharides in the vesicles.

For conjugation to CTF1232, the vesicles were oxidised in 100 mM sodium acetate (pH 5) with sodium periodate (20 mM for *S.* Typhimurium, 40 mM for *S. sonnei*) for 2 hours in the dark at room temperature. Oxidation in *S. Typhimurium* was preferential in rhamnose (Rha) residues, with about 30% of Rha units oxidized (calculated relative to mannose). Oxidation in *S. sonnei* impacted the core region of the LPS molecules.

500 µg oxidised vesicles (total measured protein) from either *S. Typhimurium* ΔtolR 1418 or *S. sonnei* 1790 nOMV were reacted with 500 µg CTF1232 with 1-2 mg NaBH$_3$CN at room temperature over a weekend. Based on unreacted antigen quantification after conjugation, the antigen presence on the nOMV surface was calculated as <36% in *S. Typhimurium* and <31% in *S. sonnei*.

The results showed that reductive amination chemistry is suitable for conjugation of polypeptide antigens to vesicles. CTF1232 antigen was conjugated to the oxidised LPS of the two vesicles.

Figure 3:
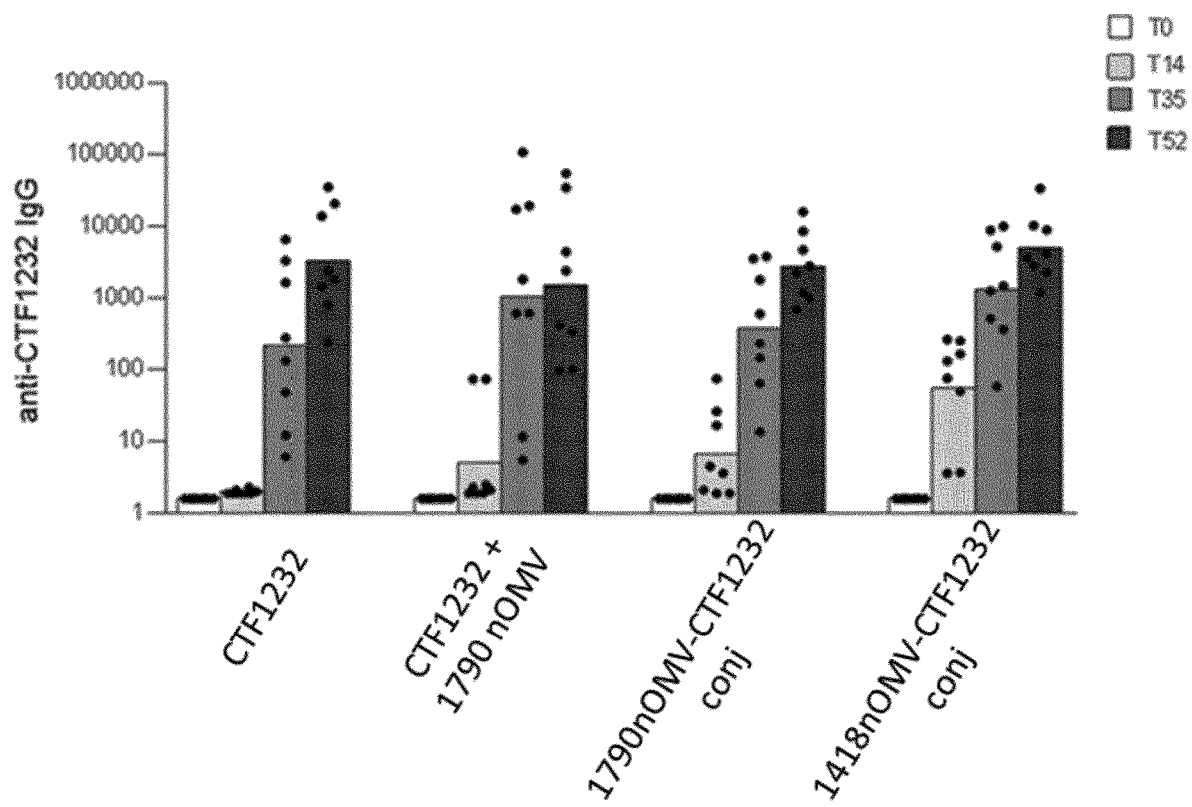
FIG. 3 shows anti-CTF1232 IgG titers after immunisation with CTF1232 polypeptide conjugated to various carriers (formulated with Alhydrogel). CD1 female mice, 5 weeks old (8 per group) were vaccinated intranasally with 30 µl of vaccine (15 µl per nostril) at study days 0, 21 and 38. Sera were collected at days 0, 14, 35 and 52. Dose was 0.5 µg CTF1232.

Mice were immunised with the protein alone, a mixture of the protein and *Shigella* nOMV, or the conjugates. Alhydrogel adjuvant was used in all groups. Immunisations were administered intranasally on days 0, 21 & 38 and immune responses were assessed on days 0, 14, 35 and 52. Anti-CTF1232 IgG titers are in FIG. 3.

At day 14, 1418nOMV-CTF1232 conjugate was able to induce a response significantly higher than the protein alone (p=0.0005) or physically mixed with nOMV (p=0.042) (Kruskal-Wallis test with Dunn's post hoc analysis). In addition to the improvement in anti-CTF1232 titers, the conjugate has the further advantage of being a bivalent vaccine. No major differences were observed between 1790nOMV-CTF1232 and 1418nOMV-CTF1232 conjugates, meaning that both *Salmonella* and *Shigella* nOMV can work as good carriers for ETEC antigen.

Figure 4A:
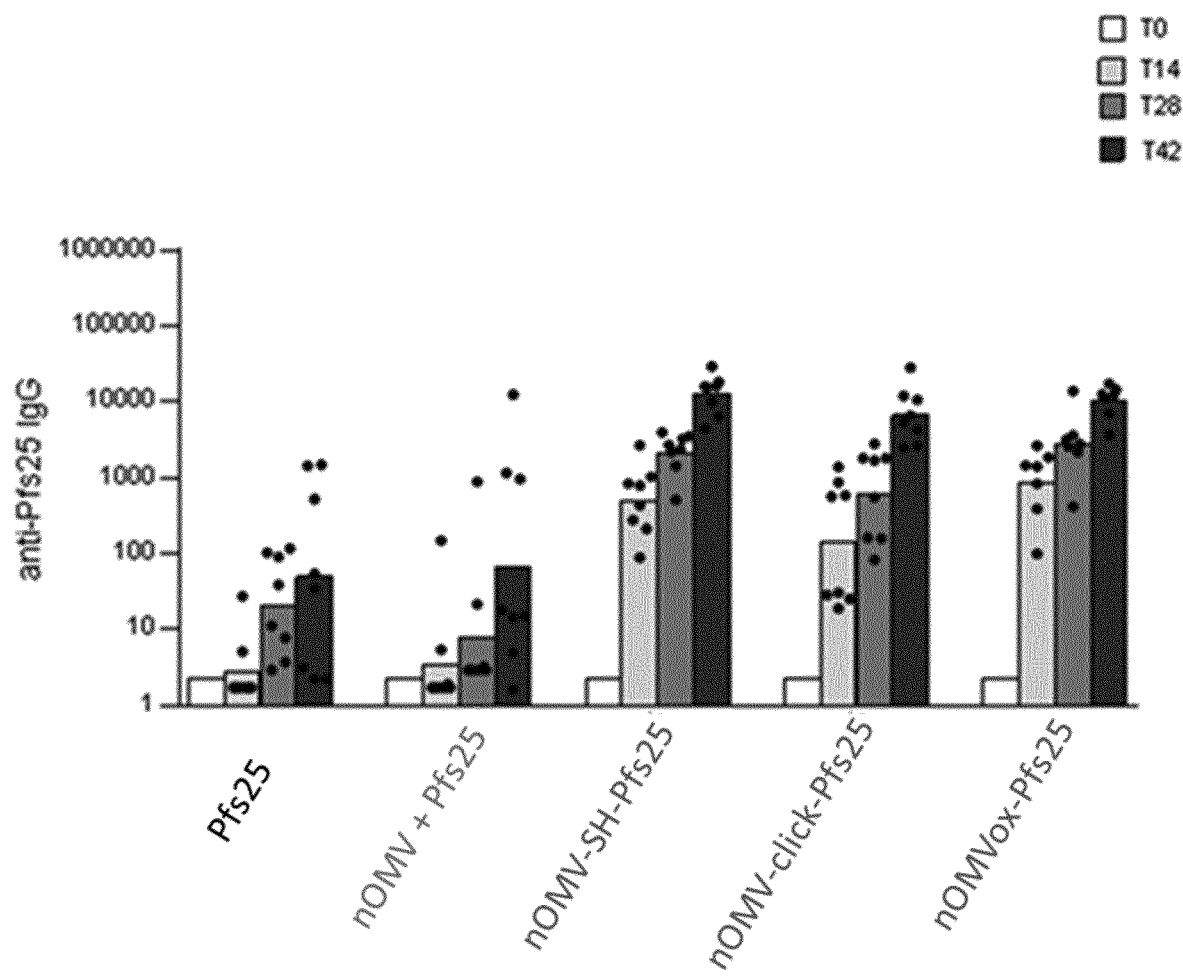
FIG. 4 show anti-Pfs25 IgG titers after immunisation with Pfs25 polypeptide conjugated to S. Typhimurium 1418 ΔtoIR nOMV compared to Pfs25 alone or physically mixed with said nOMV. CD1 female mice, 5 weeks old (8 per group) were subcutaneously immunised at days 0 and 28 with 0.1 µg Pfs25/dose (FIG. 4A, with Alhydrogel) or 1 µg Pfs25/dose (FIG. 4B, no Alhydrogel). Titres were measured at days 0, 14, 28 and 42.
FIG. 4C shows the anti-OAg IgG titers using 2 and 0.1 µg Pfs25/dose, and corresponding to 10 and 0.5 µg nOMV/dose, respectively (formulated with Alhydrogel). Again, CD1 female mice, 5 weeks old (8 per group) were subcutaneously immunised at days 0 and 28.

Example 5: nOMV-Ag Conjugation Step (Pfs25-*S. Typhimurium* nOMV Conjugation in the Presence of Na$_2$SO$_3$ Malarial antigen Pfs25 was conjugated to the *S. Typhimurium* nOMV vesicles by two different chemistries: to proteins via SH-maleimido or click chemistry; or to NaIO$_4$ oxidised OAg. For the linkage to oxidised —OAg, a 1:1 ratio of nOMV:Pfs25 was used, at a Pfs25 concentration of 2.6 mg/ml in PBS with overnight incubation at room temperature. Conjugate formation was also obtained when excess NaIO$_4$ was quenched with Na$_2$SO$_3$ (a concentration of 10 mM was used in this experiment, for 10 minutes), followed by direct addition of Pfs25 into the same pot (0.2 mg/ml final concentration). FIG. 4A shows anti-Pfs25 IgG titers in response to: the three conjugates; Pfs25 alone; or Pfs25 physically mixed with the vesicles. All the constructs were formulated with Alhydrogel. Mice were immunised subcutaneously at days 0 & 28 at 0.1 µg Pfs25/dose. Anti-Pfs25 IgG titers were measured at days 0, 14, 28 and 42.

Pfs25 alone induced an anti-Pfs25 IgG antibody response significantly lower than nOMV-SH-Pfs25 (p=0.001) and nOMV-ox-Pfs25 conjugate (p=0.0095). Pfs25 physically mixed with nOMV similarly induced a lower response than nOMV SH-Pfs25 and nOMV-ox-Pfs25 (p=0.0038 and p=0.0282 respectively) (Kruskal Wallis test with Dunn's post hoc analysis). Interestingly Pfs25 linked through the sugar component on nOMV (nOMV-ox-Pfs25 conjugate) induced a similar antibody response to Pfs25 linked to proteins on nOMV (nOMV-SH-Pfs25 and nOMV-click-Pfs25) and higher than Pfs25 alone or physically mixed to nOMV.

Sera from Pfs25-NOMV conjugates showed transmission blocking activity when tested by standard membrane-feeding assay (SMFA; transmission reducing activity >90% at 1:8 dilution and maintained at 1:16 dilution for nOMV-SH-Pfs25 and nOMV-ox-Pfs25).

The linkage of Pfs25 on nOMV did not impact on the anti-OAg IgG response. Also the conjugate obtained by reductive amination, where the chemistry used has an impact on —OAg structure and length, maintained high anti-OAg IgG titers. Accordingly, the presence of a foreign antigen on S. Typhimurium nOMV does not impact on anti-OAg IgG responses (see FIG. 4C).

In a second study, the immunogenicity of Pfs25-nOMV conjugate (produced by reductive amination) was compared to Pfs25 physically mixed to nOMV at a dose of 1 µg Pfs25 without Alhydrogel.

Figure 4B:
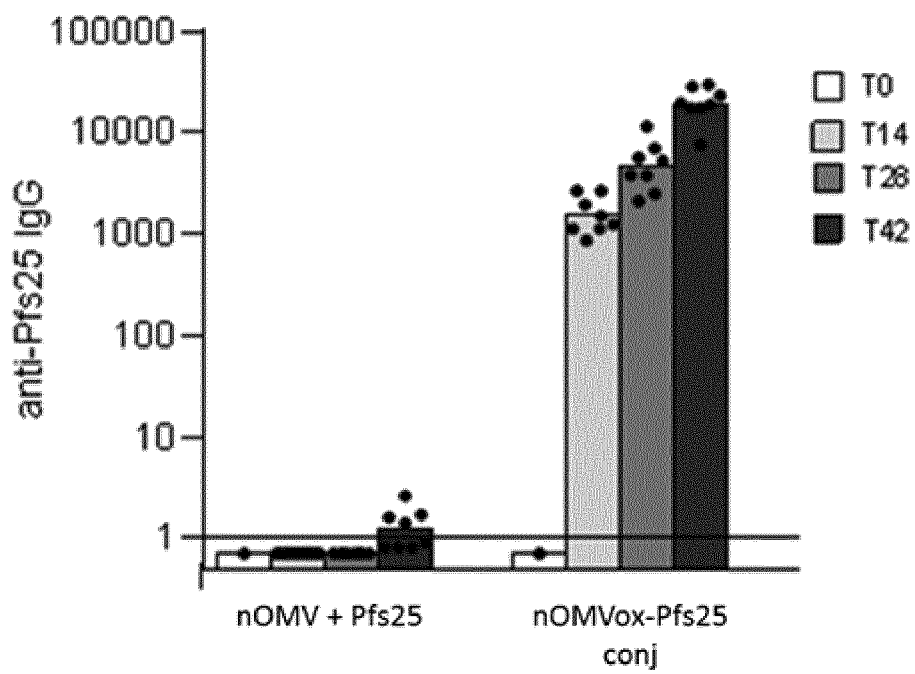
Figure 4C:
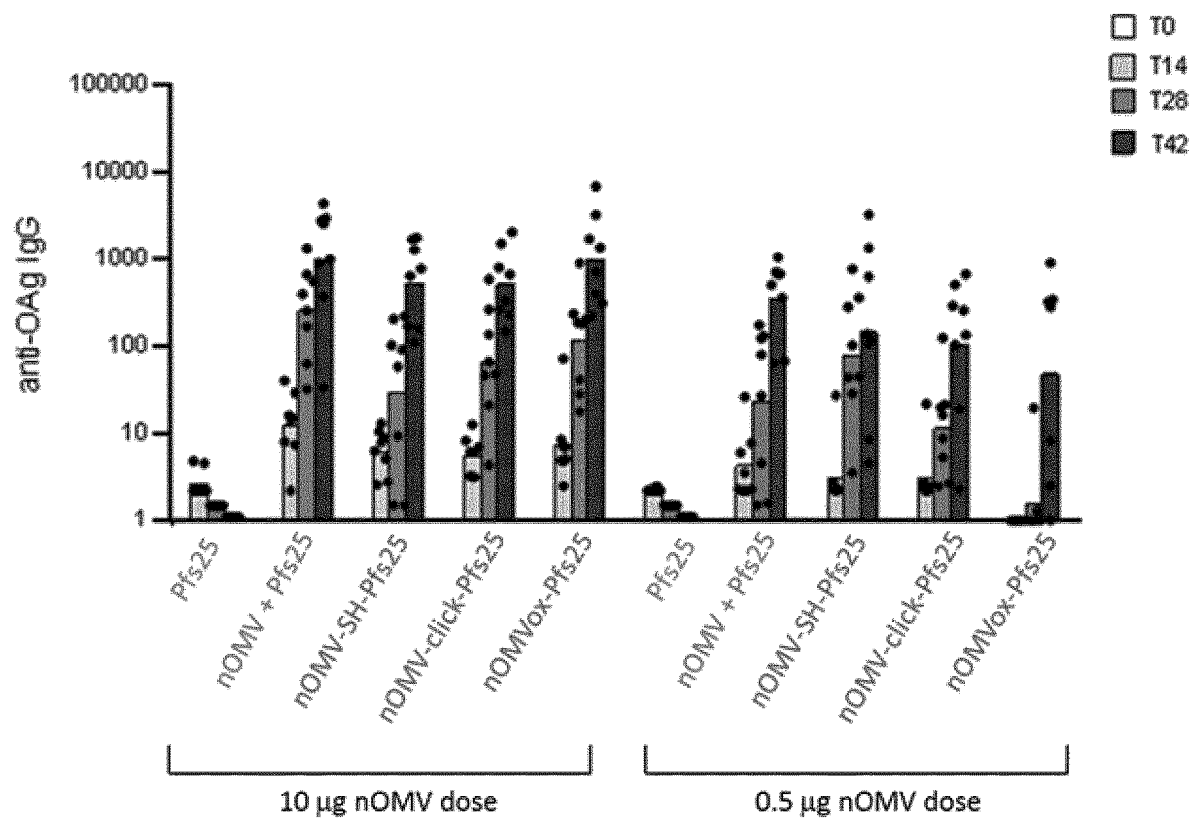

FIG. 4B shows the anti-Pfs25 IgG response induced in mice by Pfs25-nOMV conjugate compared to Pfs25 physically mixed to nOMV with no Alhydrogel, using the same immunisation schedule as for FIG. 4A.

The conjugate was able to induce a significantly higher anti-Pfs25 IgG response than the protein mixed with nOMV (p=0.0002; Mann-Whitney two-tailed analysis).

Example 6: RO6C—*S. Typhimurium* nOMV Conjugates (Recycling Step

*Plasmodium* RO6C antigen was conjugated to oxidised *S. Typhimurium* nOMV vesicles using reductive amination. A further conjugate was produced by recycling unreacted RO6C from the first conjugation batch and re-using it for conjugation. The ratio of RO6C to total protein was measured by competitive ELISA, and was 7.2% for the non-recycled conjugate and 11.1% for the recycled conjugate. For comparison, RO6C alone was used. All the constructs were formulated with Alhydrogel.

Figure 5A:
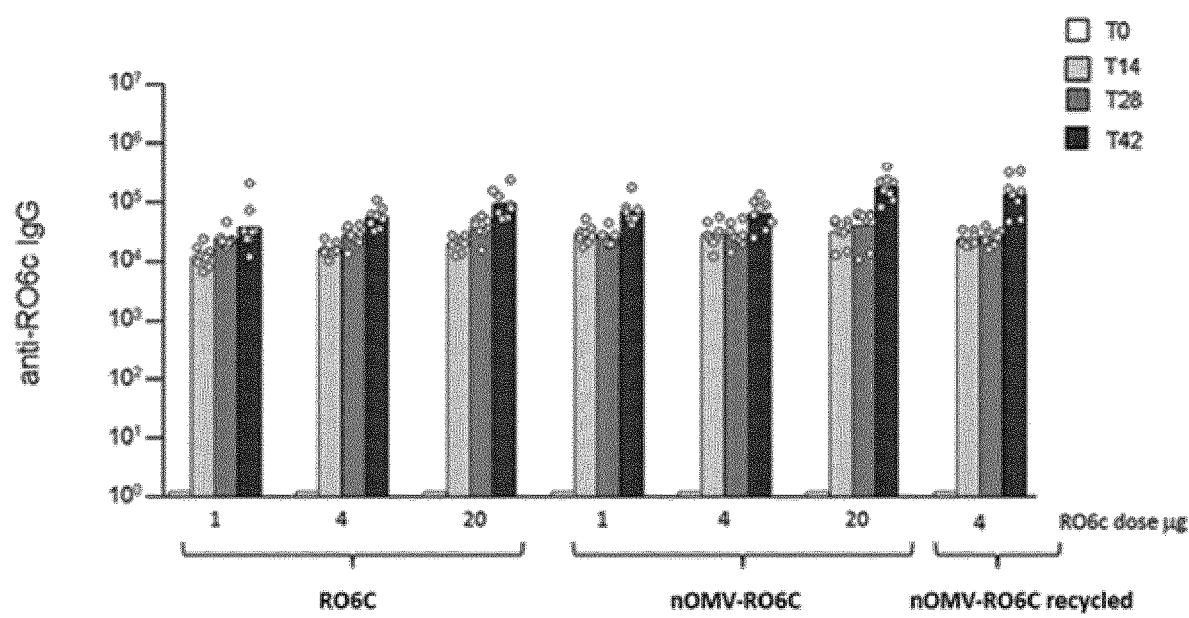
FIG. 5 show anti-RO6C IgG titers (FIG. 5A) and anti-OAg IgG titers (FIG. 5B) after immunisation with RO6C alone, or conjugated to *S. Typhimurium* 1418 ΔtoIR nOMV vesicles (formulated with Alhydrogel). A recycled conjugate was prepared by recycling unconjugated RO6C from the first conjugation batch. CD1 female mice, 5 weeks old (8 per group) were immunised subcutaneously at days 0 and 28, and doses of 1, 4 and 20 µg RO6C were used. For the conjugates, the corresponding doses of nOMV were 13 µg, 52 µg and 258 µg, respectively (4 µg RO6C and 32 µg nOMV for the recycled conjugate). IgG titers were measured at days 0, 14, 28 and 42.

Mice were immunised subcutaneously at days 0 and 28, and doses of 1, 4 and 20 µg RO6C were used. The recycled conjugate was tested at 4 µg RO6C dose. Anti-RO6C IgG titers were measured at days 0, 14, 28 and 42, and results are shown in FIG. 5A. At day 42, a higher anti-RO6C IgG response was induced by the nOMV-RO6C conjugate compared to RO6C alone (Mann Whitney test, p=0.05 at 1 µg dose, p=0.03 at 4 µg dose and p=0.04 at 20 µg dose). In addition, the nOMV-RO6C conjugate elicited an anti-RO6C IgG response in a dose dependent manner (Spearman rank, p=0.001, day 42). All the constructs (at all doses) showed the ability to boost the response (day 14-day 42). Non-recycled and recycled conjugates at 4 µg dose were compared by Mann Whitney two-tailed test, showing the ability of the recycled conjugate to induce a response not inferior to the non-recycled one.

Figure 5B:
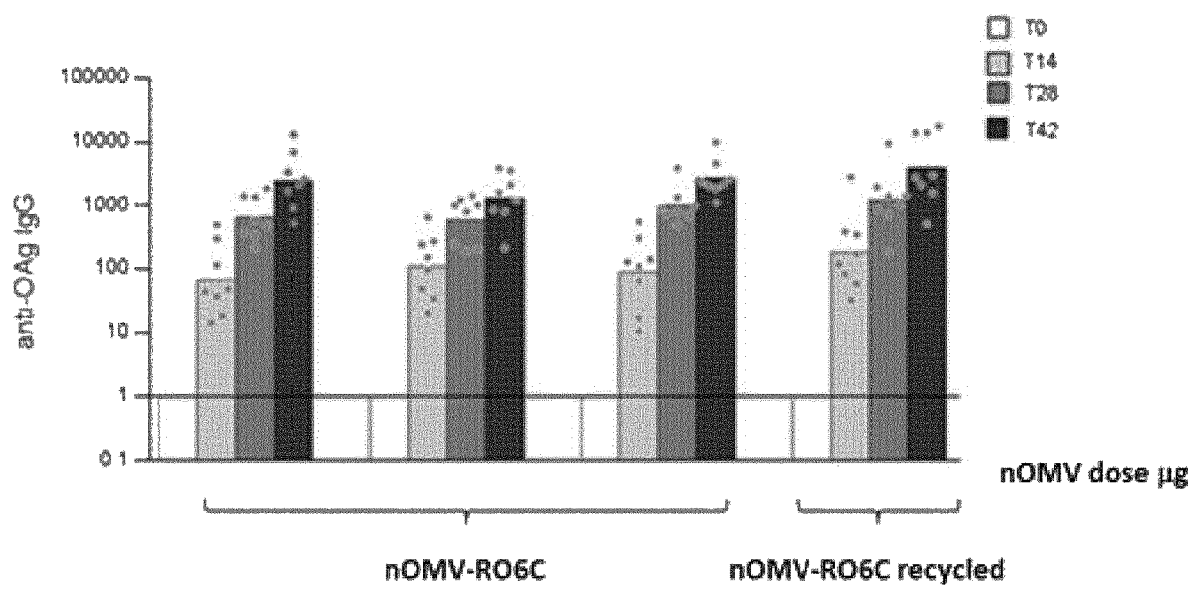

IgG titers against the —OAg were also assessed. FIG. 5B shows anti-OAg IgG titers for the non-recycled and recycled vesicles. The nOMV doses corresponding to the RO6C doses of 1, 4 and 20 µg were 13 µg, 52 µg and 258 µg, respectively. For the recycled conjugate, the nOMV dose was 32 µg (corresponding to an RO6C dose of 4 µg).

Example 7a-c: Comparative Examples

Example 7a: Reaction of dOMV (from *Neisseria meningitidis* B) with fHbp v3 (No Reaction The dOMVs of the present example have been prepared by a detergent extraction process, where the deoxycholate is used as selected detergent. The thus obtained detergent extracted vesicles have been reacted with the selected antigen (fHbp) according to process of the present invention. In particular, dOMV, at the concentration of 0.96 mg/mL, were incubated with $NaIO_4$ 10 mM for 30 minutes at room temperature, in the dark. Excess of $NaIO_4$ was quenched with $Na_2SO_3$ at a final concentration of 20 mM, for 15 minutes at room temperature. fHbp (w/w ratio of dOMV to fHbp 1:1 and with dOMV concentration of 0.335 mg/mL) and $NaBH_3CN$ (3 mg) were directly added to the reaction mixture. After overnight gently mixing at room temperature, the conjugate was purified by ultracentrifuge (110000 rpm 4° C. 1 h), re-suspended in PBS and analysed by SDS PAGE/western blot.

Example 7b: Reaction of nOMV (from *Neisseria Meningitidis* B) with fHbp v3 (Formation of the nOMV-fHbp Conjugate of the Invention The nOMVs of the present example have been prepared without using any detergent, as described in Koeberling et a. Vaccine (2014) 32:2688. The thus obtained extracted vesicles have been reacted with the selected antigen (fHbp) according to the process of the present invention. In particular, nOMV at the concentration of 0.96 mg/mL were incubated with $NaIO_4$ 5 mM for 30 minutes at room temperature, in the dark. Excess of $NaIO_4$ was quenched with $Na_2SO_3$ at a final concentration of 20 mM, for 15 minutes at room temperature. fHbp (w/w ratio of dOMV to fHbp 1:1 and with dOMV concentration of 0.335 mg/mL) and $NaBH_3CN$ (3 mg) were directly added to the reaction mixture. After overnight gently mixing at room temperature, the conjugate was purified by ultracentrifuge (110000 rpm 4° C. 1 h), re-suspended in PBS and analysed by SDS PAGE/western blot. SDS PAGE/anti-fHbp western blot analysis confirmed conjugate formation by reductive amination chemistry only with nOMV, but not with dOMV. 10% SDS page gel.

Example 7c: Reaction of nOMV (from *Salmonella*) with fHbp v1, Following the Procedure of Example 7b The same experiment as Examples 7b has been performed using nOMV from *Salmonella Typhimurium*, and similar results have been collected, obtaining the nOMV-fHbp conjugate of the invention.

Example 8: Preparation of Multi Functionalized nOMV Using $(NANP)_3$—SH-Pfs25, According to the Invention Pfs25 protein was derivatised with EMCS linker according to the following procedure. Pfs25, in PBS buffer at the concentration of 2.6 mg/mL, was added of EMCS linker (molar ratio EMCS linker to Pfs25 Lys residues of 0.3). The reaction was mixed at room temperature for 4 h. Resulting derivatised protein (Pfs25-EMCS) was purified by PD10 column against $NaH_2PO_4$ 10 mM pH 6. Analysis by MALDI-TOF MS revealed an average of 4 EMCS linkers introduced per Pfs25 molecule. $(NANP)_3$ was added to the solution of Pfs25-EMCS to have $(NANP)_3$ to EMCS linkers molar ratio of 3:1 and Pfs25 concentration of 0.7 mg/mL. The reaction was mixed at room temperature overnight. After this time, the Pfs25-$(NANP)_3$ derivative was purified by Vivaspin 10K against PBS buffer. Analysis by SDS PAGE/western blot and MALDI-TOF MS confirmed product formation. *S. Typhimurium* nOMV at the concentration of 2.1 mg/mL in $NaH_2PO_4$ 100 mM pH 6.5 were incubated with $NaIO_4$ 5 mM for 30 minutes at 25° C., in the dark. Excess of $NaIO_4$ was quenched with $Na_2SO_3$ at a final concentration of 10 mM, for 10 minutes at room temperature. Pfs25-$(NANP)_3$ (w/w ratio of nOMV to Pfs25-$(NANP)_3$ 1:1 and with nOMV concentration of 0.45 mg/mL) and $NaBH_3CN$ were directly added to the reaction mixture. After overnight gently mixing at room temperature, the conjugate was purified by ultracentrifuge (110000 rpm 4° C. 30 min), re suspended in PBS and analysed by SDS PAGE/western blot, that confirmed conjugate formation.

Figure 6A:
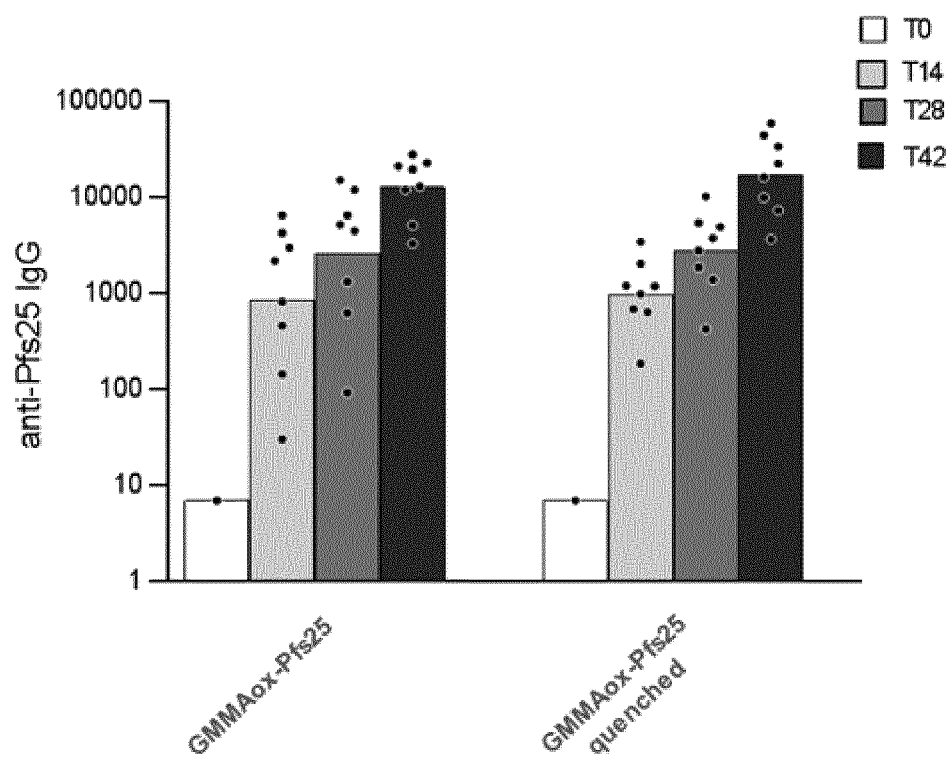
FIG. 6a: Anti-Pfs25 IgG response induced in mice (200 µL per dose SC injected at days 0 and 28, bleeds at days 0, 14, 27 and 42) by nOMV conjugates of the invention produced by conjugating *S. Typhimurium* nOMV with Pfs25 antigen, with or without quenching reaction, according to the embodiments of the invention.
Figure 6B:
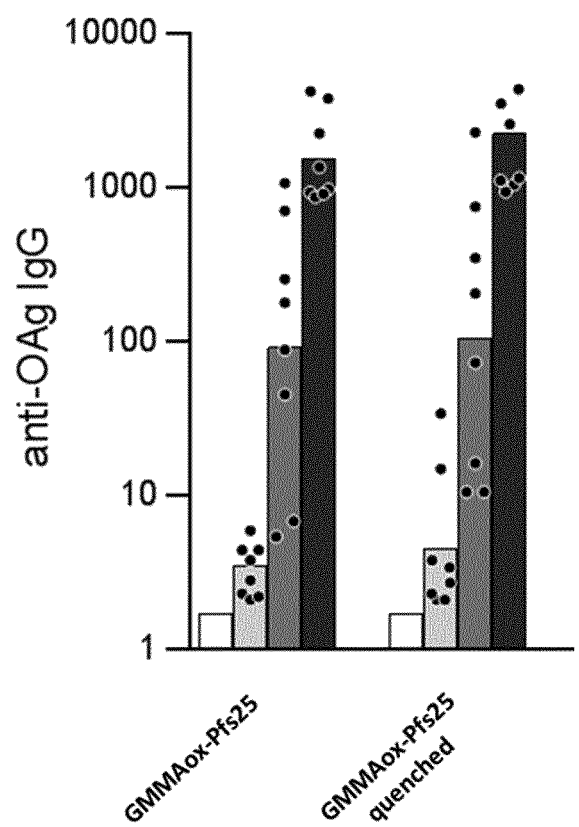
FIG. 6b: Anti-OAg response induced in mice (200 µL per dose SC injected at days 0 and 28, bleeds at days 0, 14, 27 and 42) by nOMV conjugates of the invention produced by conjugating *S. Typhimurium* nOMV with Pfs25 antigen, with or without quenching reaction, according to the embodiments of the invention.

Example 9: In-Vivo Data of the Conjugates of the Invention Obtained by Conjugating a *S. Typhimurium* nOMV Particle to Pfs25 Antigen with or without Quenching, According to the Embodiments of the Invention CD1 female mice were immunised subcutaneously at days 0 and 28 with 2.5 µg total protein S. Typhimurium nOMV particles conjugated to Pfs25 antigen with or without the quenching step (see Example 5). Both conjugates showed a Pfs25 to total protein w/w ratio close to 20% by competitive ELISA and were adsorbed on Alhydrogel (0.7 mg/mL $Al^{3+}$). Anti-Pfs5 and anti-OAg IgG titers were measured at days 0, 14, 27 and 42. At all the time points the two conjugates induced similar anti-Pfs25 IgG response (Mann Whitney test), as shown in FIG. 6a. Also, the conjugates were able to induce similar anti-OAg IgG response, as indicated in FIG. 10b. The step of quenching in the conjugation by reductive amination can be introduced with no impact on the immune response induced in mice, thus avoiding GMMA oxidation intermediate purification.

Example 10: Reaction of nOMV (from *Neisseria meningitidis* B) with MenC (Formation of the nOMV-MenC Conjugate of the Invention MenC polysaccharide was solubilised in AcONa 100 mM pH 4.5 at the concentration of 40 mg/mL. ADH linker and $NaBH_3CN$ were added with a w/w ratio 1:1.2:1.2 MenC/ADH/$NaBH_3CN$ respectively. The mixture was heated at 30° C. overnight, and then desalted by G10 column. Characterization by TNBS calorimetric method and HPAEC-PAD showed 100% derivatization.

MenB GMMA overexpressing fHbp, at the concentration of 8.5 mg/mL in $NaH_2PO_4$ 100 mM pH 6, were incubated with $NaIO_4$ 5 mM for 30 minutes at room temperature, in the dark. Excess of $NaIO_4$ was quenched with $Na_2SO_3$ at a final concentration of 10 mM, for 15 minutes at room temperature. MenC oligosaccharide, previously terminally derivatised with ADH linker (w/w ratio of GMMA to MenC 1:10 and with GMMA concentration of 7.7 mg/mL) and $NaBH_3CN$ were directly added to the reaction mixture. After overnight gently mixing at room temperature, the conjugate was purified by ultracentrifuge (110000 rpm 4° C. 1 h) and re-suspended in PBS. Analysis by SDS PAGE/western blot confirmed conjugate formation and analysis by micro BCA and HPAEC-PAD revealed a weight ratio of MenC polysaccharide to protein equal to 0.11.

Example 11: Reaction of nOMV (from *Neisseria Meningitidis* B) with MenA (Formation of the nOMV-MenA Conjugate of the Invention MenA OS was solubilised in AcONa 100 mM pH 6.5 at the concentration of 40 mg/mL. ADH linker and NaBH$_3$CN were added with a w/w ratio 1:1.2:1.2 MenA/ADH/NaBH$_3$CN respectively. The mixture was heated at 30° C. for 5 days, then desalted by G10 column. Characterization by TNBS colorimetric method and HPAEC-PAD showed 90% derivatization. Conjugation to MenB GMMA overexpressing fHbp was performed as described for MenC polysaccharide.

Example 11: Preparation of Conjugates of nOMV (from *Neisseria Meningitidis* B) with MenA and MenC Same conjugation conditions described for the synthesis of MenA- and MenC-MenB GMMA conjugates were used for conjugation of both polysaccharides on same GMMA particle. GMMA were oxidised as previously described and, after quenching with Na$_2$SO$_3$, MenA-ADH and MenC-ADH were added simultaneously with a w/w ratio 8:8:1 MenA/MenC/GMMA respectively.

The invention claimed is:

1. An immunogenic conjugate comprising a native outer membrane vesicle (nOMV), having at least a surface saccharide moiety connected to at least an antigen.

2. The immunogenic conjugate according to claim 1, comprising a nOMV having at least a surface saccharide moiety connected to a first antigen, wherein said first antigen is connected to a second different antigen.

3. The immunogenic conjugate according to claim 1, comprising a nOMV having at least a surface saccharide moiety connected to a first antigen, and at least another surface saccharide moiety connected to a second different antigen.

4. The immunogenic conjugate according to claim 1, wherein said nOMV is an intact membrane vesicle.

5. The immunogenic conjugate according to claim 1, wherein said nOMV is a spontaneously-venerated nOMV from wild type bacteria or from genetically-modified bacterial strains.

6. The immunogenic conjugate according to claim 1, wherein said nOMV is *Neisseria, Shigella, Salmonella*

*enterica* serovars, *Haemophilus influenzae, Vibrio cholerae, Bordetella pertussis, Mycobacterium smegmatis, Mycobacterium bovis* BCG, *Escherichia coli, Bacteroides, Pseudomonas aeruginosa, Helicobacter pylori, Brucella melitensis Campylobacter jejuni, Actinobacillus actinomycetemcomitans, Xenorhabdus nematophilus, Moraxella catarrhalis,* or *Borrelia burgdorferi* nOMV.

7. The immunogenic conjugate according to claim 1, wherein the antigen is an immunogenic polypeptide or a capsular polysaccharide.

8. The immunogenic conjugate according to claim 1, wherein said nOMV and antigen are from the same or different bacterial strain.

9. The immunogenic conjugate according to claim 1, wherein
   i) said nOMV is a *Salmonella Typhimurium* nOMV and said at least one antigen is *Neisseria meningitidis* fHbp;
   ii) said nOMV is a *Salmonella Typhimurium* nOMV and said at least one antigen is *Plasmodium falciparum*: CSP;
   iii) said nOMV is a *Salmonella Typhimurium* nOMV and said at least one antigen is *Plasmodium falciparum*Pfs25;
   iv) said nOMV is a *Salmonella Typhimurium* nOMV and said at least one antigen is *Plasmodium falciparum*RO6C;
   v) said nOMV is a *Salmonella Typhimurium* nOMV and said at least one antigen is *Plasmodium falciparum* RO10C;
   vi) said nOMV is a *Salmonella Typhimurium* nOMV and said at least one antigen is *Escherichia coli* CTF1232;
   vii) said nOMV is a *Salmonella Typhimurium* nOMV and said at least one antigen is S. *Typhi* Vi saccharide;
   viii) said nOMV is a *Neisseria meningitidis* nOMV and said at least one antigen is *Neisseria meningitidis* fHbp;
   ix) said nOMV is a *Neisseria meningitidis* nOMV and said at least one antigen is Poly-rhamnose oligosaccharide;
   x) said nOMV is a *Shigella* nOMV and said at least one antigen is *Escherichia coli* CTF1232;
   xi) said nOMV is a *Neisseria meningitidis* B nOMV and said at least one antigen is Capsular saccharide from MenA; or
   xii) said nOMV is a *Neisseria meningitidis* B nOMV and said at least one antigen is Capsular saccharide from MenC.

10. The immunogenic conjugate of claim 9, wherein said nOMV is a *Neisseria meningitidis* B nOMV and said at least one antigen is Capsular saccharide from MenA or said nOMV is a *Neisseria meningitidis* B nOMV and said at least one antigen is Capsular saccharide from MenC.

11. The immunogenic conjugate of claim 2, wherein said first antigen is Pfs25, and said second antigen is (NANP)$_3$.

12. The immunogenic conjugate of claim 2, wherein said first antigen is a capsular saccharide from MenA, and said second antigen is a capsular saccharide from MenC.

13. The immunogenic conjugate according to claim 1, wherein the nOMV saccharide moiety and the at least one antigen are connected together via a bivalent linker.

14. The immunogenic conjugate according to claim 1, wherein said nOMV is a GMMA vesicle.

15. A process for preparing the immunogenic conjugate according to claim 1, comprising the steps of:
   i) activating at least a nOMV surface saccharide moiety, and
   ii) connecting the thus obtained activated saccharide to at least one antigen, via a divalent linker.

16. An immunogenic composition comprising an immunogenic conjugate according to claim 1 and at least one pharmaceutically acceptable carrier or excipient.

17. A method of inducing an immune response in a vertebrate in need thereof, the method comprising administering to the vertebrate an effective amount of the immunogenic conjugate of claim 1.

18. A vaccine comprising the immunogenic conjugate of claim 1.

19. A method of making an immunogenic conjugate according to claim 1, comprising connecting a saccharide moiety on an nOMV surface to an antigen.

20. A method of inducing an immune response in a vertebrate in need thereof, the method comprising administering to the vertebrate an effective amount of the immunogenic composition of claim 16.

21. A vaccine comprising the immunogenic composition of claim 16 and an adjuvant.

\* \* \* \* \*

SEQUENCE LISTING

```
<160> NUMBER OF SEQ ID NOS: 14

<210> SEQ ID NO 1
<211> LENGTH: 247
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 2
```

<211> LENGTH: 488
<212> TYPE: PRT
<213> ORGANISM: Neisseria meningitidis

<400> SEQUENCE: 2

```
Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
            195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
    290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
    370                 375                 380

Leu His Phe His Thr Glu Asn Gly Arg Pro Tyr Pro Thr Arg Gly Arg
```

```
                385                 390                 395                 400
        Phe Ala Ala Lys Val Asp Phe Gly Ser Lys Ser Val Asp Gly Ile Ile
                        405                 410                 415

Asp Ser Gly Asp Asp Leu His Met Gly Thr Gln Lys Phe Lys Ala Ala
                        420                 425                 430

Ile Asp Gly Asn Gly Phe Lys Gly Thr Trp Thr Glu Asn Gly Ser Gly
                        435                 440                 445

Asp Val Ser Gly Lys Phe Tyr Gly Pro Ala Gly Glu Glu Val Ala Gly
                        450                 455                 460

Lys Tyr Ser Tyr Arg Pro Thr Asp Ala Glu Lys Gly Gly Phe Gly Val
        465                 470                 475                 480

Phe Ala Gly Lys Lys Glu Gln Asp
                        485

<210> SEQ ID NO 3
<211> LENGTH: 362
<212> TYPE: PRT
<213> ORGANISM: Neisseria meningitidis

<400> SEQUENCE: 3

Met Lys His Phe Pro Ser Lys Val Leu Thr Thr Ala Ile Leu Ala Thr
        1               5                   10                  15

Phe Cys Ser Gly Ala Leu Ala Ala Thr Ser Asp Asp Val Lys Lys
                        20                  25                  30

Ala Ala Thr Val Ala Ile Val Ala Ala Tyr Asn Asn Gly Gln Glu Ile
                        35                  40                  45

Asn Gly Phe Lys Ala Gly Glu Thr Ile Tyr Asp Ile Gly Glu Asp Gly
                        50                  55                  60

Thr Ile Thr Gln Lys Asp Ala Thr Ala Ala Asp Val Glu Ala Asp Asp
        65                  70                  75                  80

Phe Lys Gly Leu Gly Leu Lys Lys Val Val Thr Asn Leu Thr Lys Thr
                        85                  90                  95

Val Asn Glu Asn Lys Gln Asn Val Asp Ala Lys Val Lys Ala Ala Glu
                        100                 105                 110

Ser Glu Ile Glu Lys Leu Thr Thr Lys Leu Ala Asp Thr Asp Ala Ala
                        115                 120                 125

Leu Ala Asp Thr Asp Ala Ala Leu Asp Glu Thr Thr Asn Ala Leu Asn
                        130                 135                 140

Lys Leu Gly Glu Asn Ile Thr Thr Phe Ala Glu Thr Lys Thr Asn
        145                 150                 155                 160

Ile Val Lys Ile Asp Glu Lys Leu Glu Ala Val Ala Asp Thr Val Asp
                        165                 170                 175

Lys His Ala Glu Ala Phe Asn Asp Ile Ala Asp Ser Leu Asp Glu Thr
                        180                 185                 190

Asn Thr Lys Ala Asp Glu Ala Val Lys Thr Ala Asn Glu Ala Lys Gln
                        195                 200                 205

Thr Ala Glu Glu Thr Lys Gln Asn Val Asp Ala Lys Val Lys Ala Ala
                        210                 215                 220

Glu Thr Ala Ala Gly Lys Ala Glu Ala Ala Gly Thr Ala Asn Thr
        225                 230                 235                 240

Ala Ala Asp Lys Ala Glu Ala Val Ala Ala Lys Val Thr Asp Ile Lys
                        245                 250                 255

Ala Asp Ile Ala Thr Asn Lys Ala Asp Ile Ala Lys Asn Ser Ala Arg
                        260                 265                 270
```

Ile Asp Ser Leu Asp Lys Asn Val Ala Asn Leu Arg Lys Glu Thr Arg
       275                 280                 285

Gln Gly Leu Ala Glu Gln Ala Leu Ser Gly Leu Phe Gln Pro Tyr
290                 295                 300

Asn Val Gly Arg Phe Asn Val Thr Ala Ala Val Gly Gly Tyr Lys Ser
305                 310                 315                 320

Glu Ser Ala Val Ala Ile Gly Thr Gly Phe Arg Phe Thr Glu Asn Phe
                325                 330                 335

Ala Ala Lys Ala Gly Val Ala Val Gly Thr Ser Ser Gly Ser Ser Ala
                340                 345                 350

Ala Tyr His Val Gly Val Asn Tyr Glu Trp
                355                 360

<210> SEQ ID NO 4
<211> LENGTH: 174
<212> TYPE: PRT
<213> ORGANISM: Neisseria meningitidis

<400> SEQUENCE: 4

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170

<210> SEQ ID NO 5
<211> LENGTH: 591
<212> TYPE: PRT
<213> ORGANISM: Neisseria meningitidis

<400> SEQUENCE: 5

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
            35                  40                  45

Ala Ser Ala Asn Asn Glu Glu Gln Glu Glu Asp Leu Tyr Leu Asp Pro
50                  55                  60

```
Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
```

```
                        485                 490                 495
Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 6
<211> LENGTH: 1457
<212> TYPE: PRT
<213> ORGANISM: Neisseria meningitidis

<400> SEQUENCE: 6

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270
```

-continued

```
Ile Tyr Asp Ala Gln Lys Gln Lys Trp Leu Ile Asn Gly Val Leu Gln
            275                 280                 285

Thr Gly Asn Pro Tyr Ile Gly Lys Ser Asn Gly Phe Gln Leu Val Arg
        290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Val Asn Ser
370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
        450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
        530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
        610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
        675                 680                 685

Gly Gly Gln Ala Val Val Ser Arg Asn Val Ala Lys Val Lys Gly Asp
```

```
                690             695             700
Trp His Leu Ser Asn His Ala Gln Ala Val Phe Gly Val Ala Pro His
705             710             715             720

Gln Ser His Thr Ile Cys Thr Arg Ser Asp Trp Thr Gly Leu Thr Asn
            725             730             735

Cys Val Glu Lys Thr Ile Thr Asp Asp Lys Val Ile Ala Ser Leu Thr
            740             745             750

Lys Thr Asp Ile Ser Gly Asn Val Asp Leu Ala Asp His Ala His Leu
            755             760             765

Asn Leu Thr Gly Leu Ala Thr Leu Asn Gly Asn Leu Ser Ala Asn Gly
770             775             780

Asp Thr Arg Tyr Thr Val Ser His Asn Ala Thr Gln Asn Gly Asn Leu
785             790             795             800

Ser Leu Val Gly Asn Ala Gln Ala Thr Phe Asn Gln Ala Thr Leu Asn
            805             810             815

Gly Asn Thr Ser Ala Ser Gly Asn Ala Ser Phe Asn Leu Ser Asp His
            820             825             830

Ala Val Gln Asn Gly Ser Leu Thr Leu Ser Gly Asn Ala Lys Ala Asn
            835             840             845

Val Ser His Ser Ala Leu Asn Gly Asn Val Ser Leu Ala Asp Lys Ala
850             855             860

Val Phe His Phe Glu Ser Ser Arg Phe Thr Gly Gln Ile Ser Gly Gly
865             870             875             880

Lys Asp Thr Ala Leu His Leu Lys Asp Ser Glu Trp Thr Leu Pro Ser
            885             890             895

Gly Thr Glu Leu Gly Asn Leu Asn Leu Asp Asn Ala Thr Ile Thr Leu
            900             905             910

Asn Ser Ala Tyr Arg His Asp Ala Ala Gly Ala Gln Thr Gly Ser Ala
            915             920             925

Thr Asp Ala Pro Arg Arg Ser Arg Arg Ser Arg Arg Ser Leu Leu
            930             935             940

Ser Val Thr Pro Pro Thr Ser Val Glu Ser Arg Phe Asn Thr Leu Thr
945             950             955             960

Val Asn Gly Lys Leu Asn Gly Gln Gly Thr Phe Arg Phe Met Ser Glu
            965             970             975

Leu Phe Gly Tyr Arg Ser Asp Lys Leu Lys Leu Ala Glu Ser Ser Glu
            980             985             990

Gly Thr Tyr Thr Leu Ala Val Asn Asn Thr Gly Asn Glu Pro Ala Ser
            995             1000            1005

Leu Glu Gln Leu Thr Val Val Glu Gly Lys Asp Asn Lys Pro Leu
    1010            1015            1020

Ser Glu Asn Leu Asn Phe Thr Leu Gln Asn Glu His Val Asp Ala
    1025            1030            1035

Gly Ala Trp Arg Tyr Gln Leu Ile Arg Lys Asp Gly Glu Phe Arg
    1040            1045            1050

Leu His Asn Pro Val Lys Glu Gln Glu Leu Ser Asp Lys Leu Gly
    1055            1060            1065

Lys Ala Glu Ala Lys Lys Gln Ala Glu Lys Asp Asn Ala Gln Ser
    1070            1075            1080

Leu Asp Ala Leu Ile Ala Ala Gly Arg Asp Ala Val Glu Lys Thr
    1085            1090            1095

Glu Ser Val Ala Glu Pro Ala Arg Gln Ala Gly Gly Glu Asn Val
    1100            1105            1110
```

Gly Ile Met Gln Ala Glu Glu Lys Lys Arg Val Gln Ala Asp
1115                1120                1125

Lys Asp Thr Ala Leu Ala Lys Gln Arg Glu Ala Glu Thr Arg Pro
1130                1135                1140

Ala Thr Thr Ala Phe Pro Arg Ala Arg Arg Ala Arg Arg Asp Leu
1145                1150                1155

Pro Gln Leu Gln Pro Gln Pro Gln Pro Gln Arg Asp Leu
1160                1165                1170

Ile Ser Arg Tyr Ala Asn Ser Gly Leu Ser Glu Phe Ser Ala Thr
1175                1180                1185

Leu Asn Ser Val Phe Ala Val Gln Asp Glu Leu Asp Arg Val Phe
1190                1195                1200

Ala Glu Asp Arg Arg Asn Ala Val Trp Thr Ser Gly Ile Arg Asp
1205                1210                1215

Thr Lys His Tyr Arg Ser Gln Asp Phe Arg Ala Tyr Arg Gln Gln
1220                1225                1230

Thr Asp Leu Arg Gln Ile Gly Met Gln Lys Asn Leu Gly Ser Gly
1235                1240                1245

Arg Val Gly Ile Leu Phe Ser His Asn Arg Thr Glu Asn Thr Phe
1250                1255                1260

Asp Asp Gly Ile Gly Asn Ser Ala Arg Leu Ala His Gly Ala Val
1265                1270                1275

Phe Gly Gln Tyr Gly Ile Asp Arg Phe Tyr Ile Gly Ile Ser Ala
1280                1285                1290

Gly Ala Gly Phe Ser Ser Gly Ser Leu Ser Asp Gly Ile Gly Gly
1295                1300                1305

Lys Ile Arg Arg Arg Val Leu His Tyr Gly Ile Gln Ala Arg Tyr
1310                1315                1320

Arg Ala Gly Phe Gly Gly Phe Gly Ile Glu Pro His Ile Gly Ala
1325                1330                1335

Thr Arg Tyr Phe Val Gln Lys Ala Asp Tyr Arg Tyr Glu Asn Val
1340                1345                1350

Asn Ile Ala Thr Pro Gly Leu Ala Phe Asn Arg Tyr Arg Ala Gly
1355                1360                1365

Ile Lys Ala Asp Tyr Ser Phe Lys Pro Ala Gln His Ile Ser Ile
1370                1375                1380

Thr Pro Tyr Leu Ser Leu Ser Tyr Thr Asp Ala Ala Ser Gly Lys
1385                1390                1395

Val Arg Thr Arg Val Asn Thr Ala Val Leu Ala Gln Asp Phe Gly
1400                1405                1410

Lys Thr Arg Ser Ala Glu Trp Gly Val Asn Ala Glu Ile Lys Gly
1415                1420                1425

Phe Thr Leu Ser Leu His Ala Ala Ala Lys Gly Pro Gln Leu
1430                1435                1440

Glu Ala Gln His Ser Ala Gly Ile Lys Leu Gly Tyr Arg Trp
1445                1450                1455

<210> SEQ ID NO 7
<211> LENGTH: 654
<212> TYPE: PRT
<213> ORGANISM: Neisseria meningitidis

<400> SEQUENCE: 7

Ala Thr Asn Asp Asp Asp Val Lys Lys Ala Ala Thr Val Ala Ile Ala

-continued

```
 1               5                  10                 15
Ala Ala Tyr Asn Asn Gly Gln Glu Ile Asn Gly Phe Lys Ala Gly Glu
            20                 25                 30
Thr Ile Tyr Asp Ile Asp Glu Asp Gly Thr Ile Thr Lys Lys Asp Ala
            35                 40                 45
Thr Ala Asp Val Glu Ala Asp Asp Phe Lys Gly Leu Gly Leu Lys
            50                 55                 60
Lys Val Val Thr Asn Leu Thr Lys Thr Val Asn Glu Asn Lys Gln Asn
 65                 70                 75                 80
Val Asp Ala Lys Val Lys Ala Ala Glu Ser Glu Ile Glu Lys Leu Thr
                85                 90                 95
Thr Lys Leu Ala Asp Thr Asp Ala Ala Leu Ala Asp Thr Asp Ala Ala
                100                105                110
Leu Asp Ala Thr Thr Asn Ala Leu Asn Lys Leu Gly Glu Asn Ile Thr
                115                120                125
Thr Phe Ala Glu Glu Thr Lys Thr Asn Ile Val Lys Ile Asp Glu Lys
                130                135                140
Leu Glu Ala Val Ala Asp Thr Val Asp Lys His Ala Glu Ala Phe Asn
145                150                155                160
Asp Ile Ala Asp Ser Leu Asp Glu Thr Asn Thr Lys Ala Asp Glu Ala
                165                170                175
Val Lys Thr Ala Asn Glu Ala Lys Gln Thr Ala Glu Glu Thr Lys Gln
                180                185                190
Asn Val Asp Ala Lys Val Lys Ala Ala Glu Thr Ala Ala Gly Lys Ala
                195                200                205
Glu Ala Ala Ala Gly Thr Ala Asn Thr Ala Ala Asp Lys Ala Glu Ala
                210                215                220
Val Ala Ala Lys Val Thr Asp Ile Lys Ala Asp Ile Ala Thr Asn Lys
225                230                235                240
Asp Asn Ile Ala Lys Lys Ala Asn Ser Ala Asp Val Tyr Thr Arg Glu
                245                250                255
Glu Ser Asp Ser Lys Phe Val Arg Ile Asp Gly Leu Asn Ala Thr Thr
                260                265                270
Glu Lys Leu Asp Thr Arg Leu Ala Ser Ala Glu Lys Ser Ile Ala Asp
                275                280                285
His Asp Thr Arg Leu Asn Gly Leu Asp Lys Thr Val Ser Asp Leu Arg
                290                295                300
Lys Glu Thr Arg Gln Gly Leu Ala Glu Gln Ala Ala Leu Ser Gly Leu
305                310                315                320
Phe Gln Pro Tyr Asn Val Gly Ala Thr Asn Asp Asp Val Lys Lys
                325                330                335
Ala Ala Thr Val Ala Ile Ala Ala Tyr Asn Asn Gly Gln Glu Ile
                340                345                350
Asn Gly Phe Lys Ala Gly Glu Thr Ile Tyr Asp Ile Asp Glu Asp Gly
                355                360                365
Thr Ile Thr Lys Lys Asp Ala Thr Ala Asp Val Glu Ala Asp Asp
                370                375                380
Phe Lys Gly Leu Gly Leu Lys Lys Val Val Thr Asn Leu Thr Lys Thr
385                390                395                400
Val Asn Glu Asn Lys Gln Asn Val Asp Ala Lys Val Lys Ala Ala Glu
                405                410                415
Ser Glu Ile Glu Lys Leu Thr Thr Lys Leu Ala Asp Thr Asp Ala Ala
                420                425                430
```

```
Leu Ala Asp Thr Asp Ala Ala Leu Asp Ala Thr Thr Asn Ala Leu Asn
            435                 440                 445

Lys Leu Gly Glu Asn Ile Thr Thr Phe Ala Glu Thr Lys Thr Asn
    450                 455                 460

Ile Val Lys Ile Asp Glu Lys Leu Glu Ala Val Ala Asp Thr Val Asp
465                 470                 475                 480

Lys His Ala Glu Ala Phe Asn Asp Ile Ala Asp Ser Leu Asp Glu Thr
                485                 490                 495

Asn Thr Lys Ala Asp Glu Ala Val Lys Thr Ala Asn Glu Ala Lys Gln
            500                 505                 510

Thr Ala Glu Glu Thr Lys Gln Asn Val Asp Ala Lys Val Lys Ala Ala
        515                 520                 525

Glu Thr Ala Ala Gly Lys Ala Glu Ala Ala Gly Thr Ala Asn Thr
    530                 535                 540

Ala Ala Asp Lys Ala Glu Ala Val Ala Ala Lys Val Thr Asp Ile Lys
545                 550                 555                 560

Ala Asp Ile Ala Thr Asn Lys Asp Asn Ile Ala Lys Lys Ala Asn Ser
                565                 570                 575

Ala Asp Val Tyr Thr Arg Glu Glu Ser Asp Ser Lys Phe Val Arg Ile
            580                 585                 590

Asp Gly Leu Asn Ala Thr Thr Glu Lys Leu Asp Thr Arg Leu Ala Ser
        595                 600                 605

Ala Glu Lys Ser Ile Ala Asp His Asp Thr Arg Leu Asn Gly Leu Asp
    610                 615                 620

Lys Thr Val Ser Asp Leu Arg Lys Glu Thr Arg Gln Gly Leu Ala Glu
625                 630                 635                 640

Gln Ala Ala Leu Ser Gly Leu Phe Gln Pro Tyr Asn Val Gly
                645                 650

<210> SEQ ID NO 8
<211> LENGTH: 248
<212> TYPE: PRT
<213> ORGANISM: Neisseria meningitidis

<400> SEQUENCE: 8

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
```

```
                 145                 150                 155                 160
Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 9
<211> LENGTH: 250
<212> TYPE: PRT
<213> ORGANISM: Neisseria meningitidis

<400> SEQUENCE: 9

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 10
<211> LENGTH: 171
```

<212> TYPE: PRT
<213> ORGANISM: Plasmodium falciparum

<400> SEQUENCE: 10

```
Lys Val Thr Val Asp Thr Val Cys Lys Arg Gly Phe Leu Ile Gln Met
1               5                   10                  15

Ser Gly His Leu Glu Cys Lys Cys Glu Asn Asp Leu Val Leu Val Asn
                20                  25                  30

Glu Glu Thr Cys Glu Glu Lys Val Leu Lys Cys Asp Glu Lys Thr Val
            35                  40                  45

Asn Lys Pro Cys Gly Asp Phe Ser Lys Cys Ile Lys Ile Asp Gly Asn
        50                  55                  60

Pro Val Ser Tyr Ala Cys Lys Cys Asn Leu Gly Tyr Asp Met Val Asn
65                  70                  75                  80

Asn Val Cys Ile Pro Asn Glu Cys Lys Gln Val Thr Cys Gly Asn Gly
                85                  90                  95

Lys Cys Ile Leu Asp Thr Ser Asn Pro Val Lys Thr Gly Val Cys Ser
            100                 105                 110

Cys Asn Ile Gly Lys Val Pro Asn Val Gln Asp Gln Asn Lys Cys Ser
        115                 120                 125

Lys Asp Gly Glu Thr Lys Cys Ser Leu Lys Cys Leu Lys Glu Gln Glu
130                 135                 140

Thr Cys Lys Ala Val Asp Gly Ile Tyr Lys Cys Asp Cys Lys Asp Gly
145                 150                 155                 160

Phe Ile Ile Asp Gln Glu Ser Ser Ile Cys Thr
                165                 170
```

<210> SEQ ID NO 11
<211> LENGTH: 630
<212> TYPE: PRT
<213> ORGANISM: Artificial Sequence
<220> FEATURE:
<223> OTHER INFORMATION: pfs48/45-GURLP fusion protein

<400> SEQUENCE: 11

```
Ala Glu Arg Ser Thr Ser Glu Asn Arg Asn Lys Arg Ile Gly Gly Pro
1               5                   10                  15

Lys Leu Arg Gly Asn Val Thr Ser Asn Ile Lys Phe Pro Ser Asp Asn
                20                  25                  30

Lys Gly Lys Ile Ile Arg Gly Ser Asn Asp Lys Leu Asn Lys Asn Ser
            35                  40                  45

Glu Asp Val Leu Glu Gln Ser Glu Lys Ser Leu Val Ser Glu Asn Val
        50                  55                  60

Pro Ser Gly Leu Asp Ile Asp Ile Pro Lys Glu Ser Ile Phe Ile
65                  70                  75                  80

Gln Glu Asp Gln Glu Gly Gln Thr His Ser Glu Leu Asn Pro Glu Thr
                85                  90                  95

Ser Glu His Ser Lys Asp Leu Asn Asn Asn Gly Ser Lys Asn Glu Ser
            100                 105                 110

Ser Asp Ile Ile Ser Glu Asn Asn Lys Ser Asn Lys Val Gln Asn His
        115                 120                 125

Phe Glu Ser Leu Ser Asp Leu Glu Leu Glu Asn Ser Ser Gln Asp
130                 135                 140

Asn Leu Asp Lys Asp Thr Ile Ser Thr Glu Pro Phe Pro Asn Gln Lys
145                 150                 155                 160

His Lys Asp Leu Gln Gln Asp Leu Asn Asp Glu Pro Leu Glu Pro Phe
```

```
            165                 170                 175
Pro Thr Gln Ile His Lys Asp Tyr Lys Glu Lys Asn Leu Ile Asn Glu
            180                 185                 190
Glu Asp Ser Glu Pro Phe Pro Arg Gln Lys His Lys Lys Val Asp Asn
            195                 200                 205
His Asn Glu Glu Lys Asn Val Phe His Glu Asn Gly Ser Ala Asn Gly
            210                 215                 220
Asn Gln Gly Ser Leu Lys Leu Lys Ser Phe Asp Glu His Leu Lys Asp
225                 230                 235                 240
Glu Lys Ile Glu Asn Glu Pro Leu Val His Glu Asn Leu Ser Ile Pro
                245                 250                 255
Asn Asp Pro Ile Glu Gln Ile Leu Asn Gln Pro Glu Gln Glu Thr Asn
            260                 265                 270
Ile Gln Glu Gln Leu Tyr Asn Glu Lys Gln Asn Val Glu Glu Lys Gln
            275                 280                 285
Asn Ser Gln Ile Pro Ser Leu Asp Leu Lys Glu Pro Thr Asn Glu Asp
            290                 295                 300
Ile Leu Pro Asn His Asn Pro Leu Glu Asn Ile Lys Gln Ser Glu Ser
305                 310                 315                 320
Glu Ile Asn His Val Gln Asp His Ala Leu Pro Lys Glu Asn Ile Ile
                325                 330                 335
Asp Lys Leu Asp Asn Gln Lys Glu His Ile Asp Gln Ser Gln His Asn
            340                 345                 350
Ile Asn Val Leu Gln Glu Asn Asn Ile Asn His Gln Leu Glu Pro
            355                 360                 365
Gln Glu Lys Pro Asn Ile Glu Ser Phe Glu Pro Lys Asn Ile Asp Ser
            370                 375                 380
Glu Ile Ile Leu Pro Glu Asn Val Glu Thr Glu Ile Ile Asp Asp
385                 390                 395                 400
Val Pro Ser Pro Lys His Ser Asn His Glu Thr Phe Glu Glu Glu Thr
                405                 410                 415
Ser Glu Ser Glu His Glu Glu Ala Val Ser Glu Lys Asn Ala His Glu
            420                 425                 430
Thr Val Glu His Glu Glu Thr Val Ser Gln Glu Ser Asn Pro Glu Lys
            435                 440                 445
Ala Asp Asn Asp Gly Asn Val Ser Gln Asn Ser Asn Asn Glu Leu Asn
            450                 455                 460
Glu Asn Glu Phe Val Glu Ser Glu Lys Ser Glu His Glu Ala Arg Ser
465                 470                 475                 480
Lys Pro Lys Tyr Glu Lys Lys Val Ile His Gly Cys Asn Phe Ser Ser
                485                 490                 495
Asn Val Ser Ser Lys His Thr Phe Thr Asp Ser Leu Asp Ile Ser Leu
            500                 505                 510
Val Asp Asp Ser Ala His Ile Ser Cys Asn Val His Leu Ser Glu Pro
            515                 520                 525
Lys Tyr Asn His Leu Val Gly Leu Asn Cys Pro Gly Asp Ile Ile Pro
            530                 535                 540
Asp Cys Phe Phe Gln Val Tyr Gln Pro Glu Ser Glu Glu Leu Glu Pro
545                 550                 555                 560
Ser Asn Ile Val Tyr Leu Asp Ser Gln Ile Asn Ile Gly Asp Ile Glu
                565                 570                 575
Tyr Tyr Glu Asp Ala Glu Gly Asp Asp Lys Ile Lys Leu Phe Gly Ile
            580                 585                 590
```

```
Val Gly Ser Ile Pro Lys Thr Thr Ser Phe Thr Cys Ile Cys Lys Lys
        595                 600                 605

Asp Lys Lys Ser Ala Tyr Met Thr Val Thr Ile Asp Ser Ala Arg Ser
        610                 615                 620

His His His His His His
625                 630

<210> SEQ ID NO 12
<211> LENGTH: 394
<212> TYPE: PRT
<213> ORGANISM: Artificial Sequence
<220> FEATURE:
<223> OTHER INFORMATION: Circumsporozoite Protein (CSP)

<400> SEQUENCE: 12

Met Leu Phe Gln Glu Tyr Gln Cys Tyr Gly Ser Ser Asn Thr Arg
1               5                   10                  15

Val Leu Asn Glu Leu Asn Tyr Asp Asn Ala Gly Thr Asn Leu Tyr Asn
            20                  25                  30

Glu Leu Glu Met Asn Tyr Tyr Gly Lys Gln Glu Asn Trp Tyr Ser Leu
        35                  40                  45

Lys Lys Asn Ser Arg Ser Leu Gly Glu Asn Asp Asp Gly Asn Asn Asn
    50                  55                  60

Asn Gly Asp Asn Gly Arg Glu Gly Lys Asp Glu Asp Lys Arg Asp Gly
65                  70                  75                  80

Asn Asn Glu Asp Asn Glu Lys Leu Arg Lys Pro Lys His Lys Lys Leu
                85                  90                  95

Lys Gln Pro Gly Asp Gly Asn Pro Asp Pro Asn Ala Asn Pro Asn Val
            100                 105                 110

Asp Pro Asn Ala Asn Pro Asn Val Asp Pro Asn Ala Asn Pro Asn Val
            115                 120                 125

Asp Pro Asn Ala Asn Pro Asn Ala Asn Pro Asn Ala Asn Pro Asn Ala
        130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Ala Asn Pro Asn Ala Asn Pro Asn Ala Asn Pro Asn Val
            180                 185                 190

Asp Pro Asn Ala Asn Pro Asn Ala Asn Pro Asn Ala Asn Pro Asn Ala
        195                 200                 205

Asn Pro Asn Ala Asn Pro Asn Ala Asn Pro Asn Ala Asn Pro Asn Ala
        210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255

Asn Pro Asn Ala Asn Pro Asn Ala Asn Pro Asn Ala Asn Pro Asn Lys
            260                 265                 270

Asn Asn Gln Gly Asn Gly Gln Gly His Asn Met Pro Asn Asp Pro Asn
        275                 280                 285

Arg Asn Val Asp Glu Asn Ala Asn Ala Asn Asn Ala Val Lys Asn Asn
        290                 295                 300

Asn Asn Glu Glu Pro Ser Asp Lys His Ile Glu Lys Tyr Leu Lys Lys
305                 310                 315                 320
```

```
Ile Gln Asn Ser Leu Ser Thr Glu Trp Ser Pro Cys Ser Val Thr Cys
            325                 330                 335

Gly Asn Gly Ile Gln Val Arg Ile Lys Pro Gly Ser Ala Asn Lys Pro
            340                 345                 350

Lys Asp Glu Leu Asp Tyr Glu Asn Asp Ile Glu Lys Lys Ile Cys Lys
            355                 360                 365

Met Glu Lys Cys Ser Ser Val Phe Asn Val Val Asn Ser Ser Ile Gly
        370                 375                 380

Leu Ile Leu Glu His His His His His His
385                 390

<210> SEQ ID NO 13
<211> LENGTH: 12
<212> TYPE: PRT
<213> ORGANISM: Artificial Sequence
<220> FEATURE:
<223> OTHER INFORMATION: (NANP)3 peptide from CSP

<400> SEQUENCE: 13

Asn Ala Asn Pro Asn Ala Asn Pro Asn Ala Asn Pro
1               5                   10

<210> SEQ ID NO 14
<211> LENGTH: 134
<212> TYPE: PRT
<213> ORGANISM: Escherichia coli

<400> SEQUENCE: 14

Gln Asp Gln Arg Tyr Ile Ser Ile Arg Asn Thr Asp Thr Ile Trp Leu
1               5                   10                  15

Pro Gly Asn Ile Cys Ala Tyr Gln Phe Arg Leu Asp Asn Gly Gly Asn
            20                  25                  30

Asp Glu Gly Phe Gly Pro Leu Thr Ile Thr Leu Gln Leu Lys Asp Lys
        35                  40                  45

Tyr Gly Gln Thr Leu Val Thr Arg Lys Met Glu Thr Glu Ala Phe Gly
50                  55                  60

Asp Ser Asn Ala Thr Arg Thr Thr Asp Ala Phe Leu Glu Thr Glu Cys
65                  70                  75                  80

Val Glu Asn Val Ala Thr Thr Glu Ile Ile Lys Ala Thr Glu Glu Ser
                85                  90                  95

Asn Gly His Arg Val Ser Leu Pro Leu Ser Val Phe Asp Pro Gln Asp
            100                 105                 110

Tyr His Pro Leu Leu Ile Thr Val Ser Gly Lys Asn Val Asn Leu Glu
        115                 120                 125

His His His His His His
        130
```